(12) United States Patent
Venit et al.

(10) Patent No.: US 7,388,098 B2
(45) Date of Patent: Jun. 17, 2008

(54) DYNAMIC RESOLUTION OF ISOMERS AND RESOLVED ISOMERS

(75) Inventors: John J. Venit, North Brunswick, NJ (US); Gary D. Madding, Evansville, IN (US); Victor W. Rosso, East Windsor, NJ (US); Francis J. Okuniewicz, Somerset, NJ (US); Robert P. Discordia, Monroe Township, NJ (US); Susanne Kiau, North Brunswick, NJ (US); Atul S. Kotnis, Kendall Park, NJ (US); Michael E. Randazzo, East Windsor, NJ (US); D. David Hennings, Loveland, CO (US); Jingyang Zhu, Jamesville, NY (US); Jason G. Chen, Manlius, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1235 days.

(21) Appl. No.: 09/961,932

(22) Filed: Sep. 24, 2001

(65) Prior Publication Data
US 2002/0111512 A1   Aug. 15, 2002

Related U.S. Application Data

(60) Provisional application No. 60/236,937, filed on Sep. 29, 2000.

(51) Int. Cl.
C07C 53/134   (2006.01)
C07D 233/00   (2006.01)
C07D 277/00   (2006.01)
C07B 55/00    (2006.01)

(52) U.S. Cl. ............... 548/189; 562/496; 562/401; 548/325.1

(58) Field of Classification Search ............... 562/401, 562/496, 556, 557; 548/325.1, 189
See application file for complete search history.

(56) References Cited

U.S. PATENT DOCUMENTS
5,366,272 A   11/1994   Lebrun

FOREIGN PATENT DOCUMENTS
EP   0599444 A   6/1994

(Continued)

OTHER PUBLICATIONS

FDA's Policy Statement for the Development of New Stereoisomeric Drugs (May 1, 1992).

(Continued)

Primary Examiner—Taylor Victor Oh
(74) Attorney, Agent, or Firm—Maureen P. O'Brien; Burton Rodney; Elliott Korsen

(57) ABSTRACT

Provided is a dynamic resolution method of enriching a desired isomer of an alpha-substituted carboxylic acid relative to an undesired isomer, the method comprising: (a) in a solvent, contacting the alpha-substituted carboxylic acid, wherein the alpha substitution is with a leaving group and wherein the alpha carbon is chiral, with a homochiral amine to form a salt that is partially insoluble under selected reaction conditions, wherein the homochiral amine is selected so that the solubility of the amine salt of the undesired alpha-substituted carboxylic acid is greater than that of the amine salt of the desired alpha-substituted carboxylic acid under the selected reaction conditions; (b) reacting under the selected reaction conditions the salt with a nucleophile, wherein the reacting is effective in producing a net increase in the less soluble amine salt of the alpha-substituted carboxylic acid, and wherein the selected conditions are selected to (i) promote nucleophilic substitution of the nucleophile and the leaving group or (ii) to produce the increase in the less soluble amine salt in the absence of a strong base; and (c) maintaining the reaction for a period of time effective to increase the amount of the desired alpha-substituted carboxylic acid isomer.

21 Claims, 5 Drawing Sheets

FOREIGN PATENT DOCUMENTS

| | | |
|---|---|---|
| EP | 629627 | 12/1994 |
| EP | 657453 | 1/1999 |
| JP | 96188811 | 7/1996 |
| JP | 10014590 | 1/1998 |
| JP | P2000-23693 A | 1/2000 |
| WO | WO 00/24923 A | 5/2000 |
| WO | WO 9942431 | 5/2000 |

OTHER PUBLICATIONS

Camps et al., "(R)- and (S)-3-Hydroxy-4, 4-dimethyl-1-phenyl-2-pyrrolidonone as chiral auxiliaries for the asymmetric synthesis of alpha-hydroxy acids" Tetrahedron: Aymmetry, vol. 8, No. 11, 1997, pp. 1877-1894.

Tolman et al., "Chemistry of 4-fluoroglutamic acid. Part 3. Preparation of diasteromers of 4- fluoroglutamine and 4-fluoroisoglutamine. An enzamatic access to the antipodes of amino-2-fluoro-butyric acid", Journal of Fluorine Chemistry, vol. 101, No. 1, 2000, pp. 5-10.

DYNAMIC RESOLUTION OF ISOMERS AND RESOLVED ISOMERS

RELATED APPLICATIONS

This application claims priority benefit under Title 35 § 119(e) of U.S. provisional Application No. 60/236,937, filed Sep. 29, 2000, the contents of which are incorporated herein by reference.

FIELD OF INVENTION

The present invention relates to methods of resolving the isomers of alpha-substituted carboxylic acids in a reactive process that converts at least a portion of the undesired isomer to the desired isomer.

BACKGROUND

Traditionally, synthetic chiral bioactive compounds were used in racemic form, since technology for resolving isomers was either unavailable, or impractical for use on a commercial scale. However, the bioactive component of such a racemate is typically found in only one of two or more of isomeric forms, meaning that at least half of the administered compound does not provide the intended benefit. It is also known that the opposite enantiomer of an intended drug can have a completely different therapeutic action. In some instances, the presence of the opposite enantiomer can be toxic. The biologically inactive isomers are, nonetheless, typically as bioavailable as the active isomer, and thus provide sources of risk without an offsetting benefit. Accordingly, regulators prefer some significant level of isomeric purity. See, e.g. FDA's Policy Statement for the Development of New Stereoisomeric Drugs (May 1, 1992). Technologies for resolving compounds have improved, allowing manufacturers to more readily conform to this regulatory pressure. Nonetheless, the art needs additional isomer resolution techniques that are adaptable to commercial scale and are cost effective.

Classical techniques for resolving optical isomers have included preferential precipitation/crystallization of a chiral compound that is associated with, covalently or non-covalently, an auxiliary chiral resolving compound or moiety. Advances in chromatography techniques effective to resolve isomers have helped provide analytical tools, but such techniques are of somewhat limited industrial applicability due to the associated cost. Dynamic resolution techniques are available, such as methods that react a chiral compound that is covalently attached to an auxiliary chiral resolving compound, or methods that utilize an enolization and Schiff base formation to convert isomeric forms.

The invention provides a new, cost effective technique that resolves the isomeric mixture while increasing the amount of the desired isomer. The technique avoids the formation of intermediate covalent adducts with auxiliary chiral resolving moieties, where such covalent bonds can be difficult to reverse without destroying desired chemical moieties. Such intermediate adducts are particularly difficult to remove in the context of the alpha-substituted carboxylic acids used in the dynamic resolution technique described here, as the leaving groups of the alpha substitution are not well preserved in the adduct removal chemistries. The technique of the invention uses partially insoluble salts of the alpha-substituted carboxylic acids formed with chiral amine compounds, yet unexpectedly the amine moieties do not disrupt the chemistry of the dynamic resolution technique.

SUMMARY OF THE INVENTION

The invention provides a dynamic resolution method of enriching a desired isomer of an alpha-substituted carboxylic acid relative to an undesired isomer, the method comprising: (a) in a solvent, contacting the alpha-substituted carboxylic acid, wherein the alpha substitution is with a leaving group and wherein the alpha carbon is chiral, with a homochiral amine to form a salt that is partially insoluble under selected reaction conditions, wherein the homochiral amine is selected so that the solubility of the amine salt of the undesired alpha-substituted carboxylic acid is greater than that of the amine salt of the desired alpha-substituted carboxylic acid under the selected reaction conditions; (b) reacting under the selected reaction conditions the salt with a nucleophile, wherein the reacting is effective in producing a net increase in the less soluble amine salt of the alpha-substituted carboxylic acid, and wherein the selected conditions are selected to (i) promote nucleophilic substitution of the nucleophile and the leaving group or (ii) to produce the increase in the less soluble amine salt in the absence of a strong base; and (c) maintaining the reaction for a period of time effective to increase the amount of the desired alpha-substituted carboxylic acid isomer.

The method can be for preparing an alpha-substituted carboxylic acid or derivative thereof, and thereby comprise: (1) [conducting the method of claim 1 to obtain]obtaining at least 80% enantiomeric excess in the alpha-substituted carboxylic acid; and (2) isolating the alpha-substituted carboxylic acid or an acid adduct thereof or reacting the alpha-substituted carboxylic acid in a subsequent reaction. The method can further comprise: (3) reacting the alpha-substituted carboxylic acid with a nucleophile to replace the leaving group with the nucleophile.

The invention further provides a method of dynamically resolving 3,4,4-trimethyl-2,5-dioxo-1-imidazolidinebutanoic acid alpha-substituted with a leaving group, the method comprising: (a) in a solvent, contacting the alpha-substituted 3,4,4-trimethyl-2,5-dioxo-1-imidazolidinebutanoic acid, with a homochiral amine to form a salt that is partially insoluble under selected reaction conditions, wherein the homochiral amine is selected so that the solubility of a desired isomer of the alpha-substituted 3,4,4-trimethyl-2,5-dioxo-1-imidazolidinebutanoic acid is less than that of an opposite isomer under the selected reaction conditions; (b) reacting, under the selected reaction conditions, the salt with a nucleophile, wherein the reacting is effective in producing a net increase in the less soluble amine salt of the alpha-substituted carboxylic acid, and wherein the selected conditions are selected to (i) promote nucleophilic substitution of the nucleophile and the leaving group or (ii) to produce the increase in the less soluble amine salt in the absence of a strong base; and (c) maintaining the reaction for a period of time effective to increase the amount of the desired isomer of alpha-substituted 3,4,4-trimethyl-2,5-dioxo-1-imidazolidinebutanoic acid. The method can further include: (d) conducting a nucleophilic substitution reaction to substitute the leaving group of the alpha-substituted 3,4,4-trimethyl-2,5-dioxo-1-imidazolidinebutanoic acid with Prt-S —["–" representing a bond], where Prt is a removable thio protecting group, thereby obtaining the S★-isomer alpha substituted with Prt-S—; (e) fanning an amide bond between the carboxylic acid moiety of the substituted 3,4,4-trimethyl-2,5-dioxo-1-imidazolidinebutanoic acid and L-leucyl-N,3-dimethyl-L-valinamide; and (f) removing the protecting group to obtain (αS)-α-mercapto-3,4,4-trimethyl-2,5-dioxo-1-imidazolinebutanoyl-L-leucyl-N,3-dimethyl-L-valinamide.

The invention also provides a dynamic resolution method of enriching a desired isomer of an alpha-substituted carboxylic acid relative to an undesired isomer, the method comprising: (a) in a solvent, contacting the alpha-substituted carboxylic acid, wherein the alpha substitution is with a leaving group and wherein the alpha carbon is chiral, with a homochiral amine to form a salt; said homochiral amine being selected so that the solubility of the amine salt of the undesired alpha-substituted carboxylic acid is greater than that of the amine salt of the desired alpha-substituted carboxylic acid under selected reaction conditions; (b) identifying the polymorph of said salt; (c) determining the difference in solubility of the diastereomers of said polymorph; (d) increasing the difference in solubility of said diastereomers by converting said polymorph into a second polymorph; (e) reacting under said selected reaction conditions said salt with a nucleophile, wherein the reacting is effective in producing a net increase in the less soluble amine salt of the alpha-substituted carboxylic acid, and wherein said selected conditions are selected to (i) promote nucleophilic substitution of the nucleophile and the leaving group or (ii) to produce the increase in the less soluble amine salt in the absence of a strong base; and (f) maintaining the reaction for a period of time effective to increase the amount of the desired alpha-substituted carboxylic acid isomer. In a preferred embodiment, converting said polymorph into a second polymorph is accomplished by slurrying said polymorph in a solvent at elevated temperatures.

The invention further provides a method of dynamically resolving 3-phenylpropanoic acid alpha-substituted with a leaving group, the method comprising: (a) in a solvent, contacting the alpha-substituted 3-phenylpropanoic acid, with a homochiral amine to form a salt that is partially insoluble under selected reaction conditions, wherein the homochiral amine is selected so that the solubility of a desired isomer of the alpha substituted 3-phenylpropanoic acid is greater than that of an opposite isomer under the selected reaction conditions; (b) reacting, under the selected reaction conditions, the salt with a nucleophile, where the nucleophile is the anion equivalent of the leaving group, under conditions selected to promote nucleophilic substitution of the nucleophile and the leaving group; and (c) maintaining the reaction for a period of time effective to increase the amount of the desired isomer of alpha-substituted 3-phenylpropanoic acid.

Further provided is a compound selected from:
(R) or (S)-α-bromo-3,4,4-trimethyl-2,5-dioxo-1-imidazolidinebutanoic acid as a salt with a homochiral amine which is not quinine;
(R) or (S)-α-(benzoylthio)-3,4,4-trimethyl-2,5-dioxo-1-imidazolidinebutanoic acid as a salt with a homochiral amine which is not quinine.

Also provided is a method of preparing (2R)-2-bromo-3-phenylpropanoic acid from (L)-phenylalanine, the method comprising: (a) converting (L)-phenylalanine to form (2S)-2-bromo-3-phenylpropanoic acid; (b) contacting (2S)-2-bromo-3-phenylpropanoic acid in a solvent with a homochiral amine to form a salt that is partially insoluble under selected reaction conditions, wherein the homochiral amine is selected so that the solubility of the amine salt of the (2S)-2-bromo-3-phenylpropanoic acid is greater than that of the amine salt of the (2R)-2-bromo-3-phenylpropanoic acid under the selected reaction conditions; (c) reacting under the selected reaction conditions the amine salts with a bromide, wherein the reacting is effective in producing a net increase in the amine salt of (2R)-2-bromo-3-phenylpropanoic acid, and wherein the selected conditions are selected to (i) promote nucleophilic racemization of (2S)-2-bromo-3-phenylpropanoic acid or (ii) produce the increase in (2R)-2-bromo-3-phenylpropanoic acid in the absence of a strong base; and (d) maintaining the reaction for a period of time effective to increase the amount of (2R)-2-bromo-3-phenylpropanoic acid.

Still further provided is a method of preparing a desired enantiomer of an alpha substituted carboxylic acid from a bulk sourced amino acid, the method comprising: (a) converting an undesired enantiomer of an alpha-amino carboxylic acid to form an undesired enantiomer of an alpha-substituted carboxylic acid, wherein the alpha substitution is with a leaving group and the alpha carbon is chiral; (b) contacting the undesired enantiomer of the alpha-substituted carboxylic acid, with a homochiral amine to form a salt that is partially insoluble under selected reaction conditions, wherein the homochiral amine is selected so that the solubility of the amine salt of the undesired enantiomer is greater than that of the amine salt of the desired enantiomer under the selected reaction conditions; (c) reacting under the selected reaction conditions the amine salts with a nucleophile, wherein the reacting is effective in producing a net increase in the amine salt of the desired enantiomer of the alpha-substituted carboxylic acid, and wherein the selected conditions are selected to (i) promote nucleophilic substitution of the nucleophile and the leaving group or (ii) produce the increase in the desired enantiomer of the alpha-substituted carboxylic acid in the absence of a strong base; and (d) maintaining the reaction for a period of time effective to increase the amount of the desired enantiomer of the alpha-substituted carboxylic acid.

Also provided is a compound of the formula:

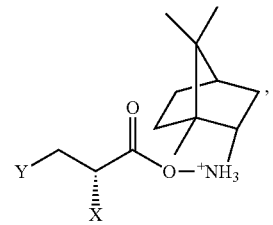

wherein X is a halogen selected from the group consisting of chlorine, bromine and iodine; and Y is selected from the group consisting of phenyl and substituted phenyl; and a compound of the formula:

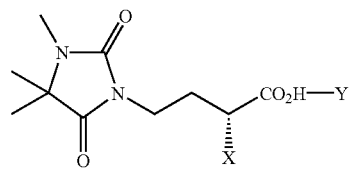

wherein X is selected from the group consisting of chlorine, bromine, iodine and thiobenzoate; and Y is an amine selected from the group consisting of S-methylbenzylamine and (1R,2S)-(-)-2-amino-1,2-diphenylethanol.

DETAILED DESCRIPTION OF THE INVENTION

Figure 1:
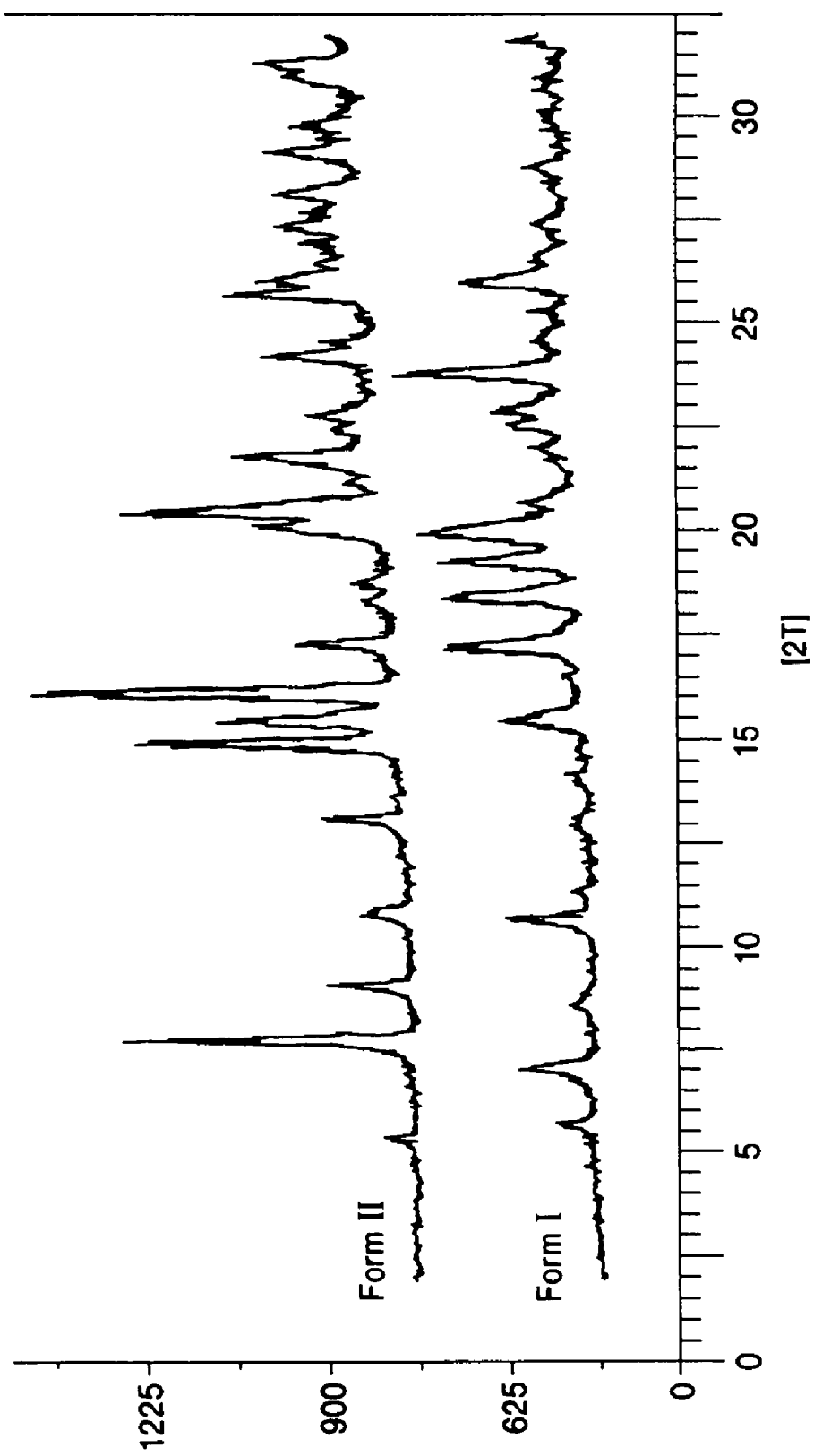
FIG. 1 shows the X-Ray Powder Diffraction patterns of Polymorph Form I and II of the salt of α-Bromo-3,4,4-trimethyl-2,5-dioxo-1-imidazolidinebutanoic acid.

In accordance with the present invention, a dynamic resolution has been developed that allows the practical preparation of chiral α-substituted carboxylic acids in high enantiomeric excess. The process involves the conversion of racemic α-substituted carboxylic acids to enantiomerically enriched or enantiomerically pure chiral α-substituted carboxylic acids. The products obtained from this process can be useful intermediates for the synthesis of products having pharmaceutical applications as well as useful endproducts. The process is simple, and can be executed using a one pot conversion involving moderate temperatures. In contrast to the dynamic resolution of the invention, widely accepted methods exist which require covalent attachment of an acid or acid derivative to a chiral resolving adduct. No such covalent attachment is believed to be required in the present invention. Additionally, the yields of the enantiomerically pure α-substituted acid are high (e.g., 60-95%, or higher). Moreover, the products obtained from the reaction are of high quality with respect to both absolute purity and enantiomeric purity. Finally, the process is economical as a one pot process with minimal chemical usage. The process can be carried to a high degree of completion, utilizing both isomers of the starting racemic material. The recyclable chiral resolving adduct is recovered by a simple process, thereby helping to minimize cost and reduce waste.

The transformation of racemic α-substituted carboxylic acids to α-substituted carboxylic acids of higher enantiomeric purity is begun with a pair of diastereomeric salts (2R and 2S) of a racemic α-substituted carboxylic acid and a homochiral amine. See Scheme 1 below. The α-substitution is with a leaving group, denoted in Scheme 1 as "X." The process is carried out as a slurry whereby the desired isomer (2R in the example shown in Scheme 1) is less soluble than the undesired isomer (2S) in the solvent system of the process. Because of the differential solubilities of the diastereomeric salts, the precipitate is enriched in the desired diastereomer (2R) while the supernatant is enriched in the undesired diastereomer (2S). The degree of enrichment can be relatively small, with the process still providing a useful degree of isomeric enrichment. In the supernatant the presence of at least a catalytic amount of nucleophile facilitates the displacement of the α-substituent. This displacement results in the conversion of the more soluble diastereomer (2S) into the less soluble diastereomer (2R). Precipitation of the excess desired diastereomer (2R) and resolution of the diminished undesired diastereomer (2S) occurs until a thermodynamic equilibrium mixture of diastereomers is achieved. In this way, a racemic α-substituted carboxylic acid is converted into a diastereomerically enriched or pure diastereomeric salt in a single reaction vessel. The pure chiral or enantiomerically enriched α-substituted carboxylic acid can be liberated from the salt and the chiral amine recovered for re-use. The product of this process can then be used in other synthetic transformations. The product of the process is sufficiently enantiomerically enriched so that the product or a product from subsequent synthetic steps can be crystallized to further improve the enantiomeric excess. In contrast to prior art methods of α epimerization of racemic α-substituted carboxylic acids, the present invention achieves the epimerization using a nucleophile rather than a strong base. Moreover, the conversion can be accomplished without substantial substitution of the leaving group with the amine of the homochiral amine.

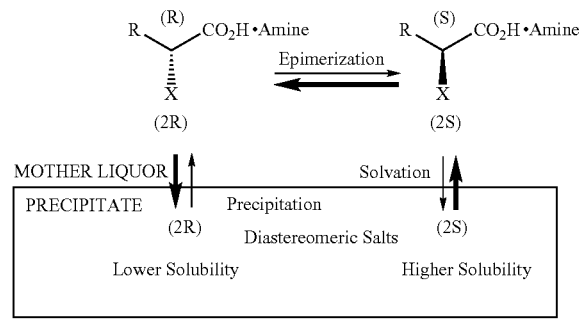

Scheme 1

A chiral α-substituted carboxylic acid with an α leaving group serves as a suitable substrate for the dynamic resolution process. The leaving group in its anionic form can also function as the nucleophile. Suitable leaving groups include, for example, halogens, and sulfur, oxygen, or nitrogen containing components. These leaving groups can include, for example, chlorides, bromides, iodides, alkanoates, benzoates, thioalkanoates, thiobenzoates, thiolates, silyl alcoholates, azides, cyanide, and the like. Typically at least a catalytic amount of the nucleophile is added to facilitate the displacement of the α-substituent. In one embodiment of the invention the nucleophile that is contacted with the α-carboxylic acid is distinct from the leaving group and, the amount added is a catalytic amount. Tetrabutylammonium bromide and potassium bromide provide useful catalytic nucleophiles.

Racemic α-substituted carboxylic acids are often commercially available or can be readily prepared. Often a ready source of the starting material can be obtained from racemic α-amino acids. For example, racemic 2-bromo-3-phenyl propanoic acid can be prepared by treating racemic phenylalanine with sodium nitrite and acid, followed by the addition of KBr.

It can be recognized that the process of the present invention can, additionally, be applicable for diastereomeric pairs of α-substituted carboxylic acids where the difference in configuration between the pair is at the α center. In this application, the starting carboxylic acid substrate has at least one other chiral center in addition to the chiral α-center. Using the process of the invention in this application, a pure diastereomer could be obtained from a diastereomeric mixture after liberation of the carboxylic acid from the chiral amine.

Suitable solvents for the transformation are chosen to effect precipitation of at least some of the desired diastereomeric salt and to allow the other member of the pair to remain dissolved in the solution. The solvents and other reaction conditions are selected to provide this effect at a temperature suitable for the stereochemistry converting epimerization reaction to occur. Combinations of solvents can be used to practice the present invention. A preferred solvent is one that has a boiling range at least greater than 50° C. and less than 120° C. A preferred solvent is a mixture of solvents, where screening experiments are used to select an appropriate mixture that achieves a favorable diastereometric solubility discrimination. Such mixtures can include, for example, mixtures of isopropyl acetate and methyl t-butyl ether.

The process is preferably carried out under mild conditions. Preferably, no strong base is added, especially in an amount effective to mediate a base-catalyzed enolization reaction. The temperature of the process is preferably below 80° C., preferably at or below 50-60° C. The time of the reaction is typically 24 to 48 hours. In a preferred embodiment, the process is accomplished by a one-pot procedure. It will of course be recognized that the temperature and solvents that may be preferable for a given dynamic resolution will very with the particular compound subjected to the resolution. For example, azide-containing compounds can be expected to effectively react at low temperatures.

Salt pair formation is achieved with a homochiral amine. A preferred amine is one that allows formation of a pair of diastereomeric salts, one member of the pair of diastereomers being at least partially insoluble in the solvent system of the process. A preferred amine is one that allows formation of a pair of diastereomers, one member of the pair being preferentially a precipitate under the reaction conditions. The precipitate can be crystalline or non-crystalline. These chiral amines can be, for example, depending on the application, S-(+)-1-cyclohexylethylamine, (−)-cis-myrtanylamine, S-benzyl-L-cysteinol, S-(−)-α,α-diphenyl-2-pyrrolidinemethanol, R-(+)-bornylamine, (1S,2R)-(+)-2-amino-1,2-diphenylethanol, (1S,2S)-(+)-pseudoephedrine, dehydroabietylamine, (−)-cinchonidine, (2S,3R)-(+)-4-dimethylamino-1,2-diphenyl-3-methyl-2-butanol, L-α-amino-ε-caprolactam, (1R,2R,3R,5S)-(−)-isopinocamphylamine, S-(−)-1-1'-binapthyl-2,2'-diamine, (1R,2S)-(−)-ephedrine, (1R,2S)-(+)-cis-1-amino-2-indanol, (−)-Sparteine, and S-(+)-α-(methoxymethyl)phenethylamine. Other exemplary amines that can be expected to be useful in effecting the invention for other alpha-substituted carboxylic acids including those used in the examples below.

A suitable amine and solvent for salt pair formation can be identified using a screening approach. In a primary screen, variable and unique combinations of chiral amines and solvent are combined in separate containers with a given α-substituted carboxylic acid. The presence of a salt as a precipitate can be determined by visual inspection after an incubation period, at a given time and temperature that models the epimerization reaction. The precipitated salts can then be evaluated by chiral HPLC to determine the enantiomeric excess. From the most promising candidate combinations from the primary screen, a secondary screen can subsequently be performed at a larger scale to determine the recovery yield of the precipitate, the extent of conversion, and purity.

Conversion progress can be monitored to determine if the process is sufficiently complete. The process is judged to be complete when the enantiomeric ratio is detected to meet the criteria set by the experimenter. This criteria is met in a preferred embodiment when the mixture is converted to a thermodynamic equilibrium mixture. A preferred method of HPLC analysis uses a chiral column to separate the enantiomers.

The less soluble diastereomeric salt from the transformation can be isolated, for example, by filtration, centrifugation, or decantation. For instance, the reaction mixture is cooled to room temperature and the resulting precipitate is recovered by filtration. The filter cake containing the product can be washed with a washing solvent such as methyl t-butyl ether.

Once isolated, the precipitated diastereomeric salt can be liberated from its complexed chiral amine by reaction with a suitably strong acid. Useful acids include methanesulfonic acid, sulfuric acid, phosphoric acid and hydrochloric acid, although other acids can be used. In a convenient liberation procedure, the precipitated diastereomeric salt is suspended in an organic solvent that is substantially immiscible with water. Water is added to the suspension. The pH of the aqueous phase is adjusted with the strong acid, and the liberated acid is extracted in the organic phase. In one embodiment of the invention, the organic extraction solvent is selected so that the liberated acid is dissolved in the solvent used for the next synthetic transformation. Methyl t-butyl ether and ethyl acetate are typical solvents for this extraction procedure. Alternatively, the acid portion can be extracted into water using a base (e.g., bicarbonate), and the amine extracted into the organic phase. If desired, the water phase can then be acidified, and the acid extracted into an organic phase.

Additionally, the salt formed upon contacting the alpha-substituted carboxylic acid with a homochiral amine may be in the form of different polymorphs. Hence, if the method of the instant invention provides inadequate dynamic resolution results, it may be due to the specific polymorph of said salt. Accordingly, it may be prudent to identify which polymorph form the salt has taken and determine whether that polymorph is desirable. To be desirable, there should be an adequate difference in the solubility of the diastereomers present in the polymorph. Identifying which polymorph, or polymorphs, are desirable should be easily accomplished by one skilled in the art. For example, powder X-ray analysis or an assay based on Ramen spectroscopy could be used to identify the polymorph. Once a polymorph is identified, the difference in the diastereomers should be determined to see if the polymorph is desireable.

The effect of the polymorph form of the salt was identified after a series of illperforming dynamic resolutions occurred. More specifically, for the salt formed from the α-Bromo-3,4,4-trimethyl-2,5-dioxo-1-imidazolidinebutanoic acid, only polymorph form I showed the required difference in the solubities of the diastereomers to allow for the dynamic resolution to take place. Further, when polymorph form II was the only polymorph form present, the resolution stalls at 50-60/50-40 (R/S). After complete resolution to 94/6 (R/S) only polymorph form I was observed by Raman spectroscopy. Hence, it was determined that complete Resolution to about 95:5 (RRS:SRS) occurs only in presence of crystal form I. In the presence of crystal form II, the resolution stalls at a diastereomeric ratio of about 60:40 (RRS:SRS). Accordingly, Example 13 provides an example of how to identify different polymorphs of the salt while Example 14 illustrates the Effect on the Resolution difference between the polymorphs. It was further determined that under certain conditions (e.g., in presence of crystal form I and/or slurrying the undesired polymorph in a solvent at elevated temperatures—in this case, heating to greater than about 60° C. for extended times in a polar solvent) undesirable polymorph form II could be converted to the desirable, thermodynamically stable, polymorph form I. Thus, Example 15 illustrates how undesired polymorph can be converted into desired polymorph.

An expedient route in the preparation of the matrix metalloprotease inhibitor (αS)-α-mercapto-3,4,4-trimethyl-2,5-dioxo-1-imidazolidinebutanoyl-L-leucyl-N,3-dimethyl-L-valinamide VI (Scheme 2 below) involves an α-substituted carboxylic acid intermediate. Metalloprotease inhibitors have utility, for example, in the treatment of pathological diseases associated with uncontrolled breakdown of connective tissues catalyzed by metalloproteases. These diseases include: rheumatoid arthritis; osteoarthritis; septic arthritis; corneal, epidermal, or gastric ulceration; tumor metastasis or invasion; periodontal disease; proteinuria; coronary thrombosis associated with plaque rupture and bone disease. Other useful indications for these inhibitors include prevention of the pathological squalae following a traumatic injury and, birth control. Efficient syntheses of VI and related compounds are needed for preparation of clinical trial material as well as for routes of manufacture for the commercial product.

The preparation of VI involves an α-bromo acid intermediate I (Scheme 2). Racemic I is converted to the enantiomerically enriched IB via the process of the present invention. Acid I is heated with chiral amine II (1R,2S)-2-amino-1,2-diphenylethanol and a catalytic amount of tetrabutylammonium bromide (TBAB) in a mixture of isopropyl acetate (i-PrOAc) and methyl t-butyl ether (MTBE). The diastereomer IA is then acidified with methanesulfonic acid (MSA) to provide the homochiral acid IB in at least 85% ee, preferably at least 87% ee (enantiomeric excess). The acid IB is then treated with thiobenzoic acid and potassium carbonate to provide the thiobenzoate intermediate III with complete inversion of the α-center. The crude thiobenzoate III is further purified by crystallization from methyl t-butyl ether and heptane to provide III with an improved ee of at least 98%, as determined by chiral HPLC analysis. The intermediate III is coupled with a dipeptide using a two step procedure. In the first step, the carboxylic acid is activated using the Vilsmeier reagent. Other suitable activation methods have been found to also be useful, such as, for example, the use of mixed anhydrides (e.g., employing isobutylchlorofomate), the use of acid chlorides, or the use of carbodiimide-mediated complings. In a second step, the activated intermediate is coupled to dipeptide IV to afford amide-linked intermediate V. Finally, the thiobenzoate protecting group of V is cleaved with 3-dimethylaminopropylamine (DPAP) and methanol in the presence of dithiothreitol (DTT) to provide metalloprotease inhibitor VI in 88% yield and in 99.8% enantiomeric purity (relative area percent, chiral assay).

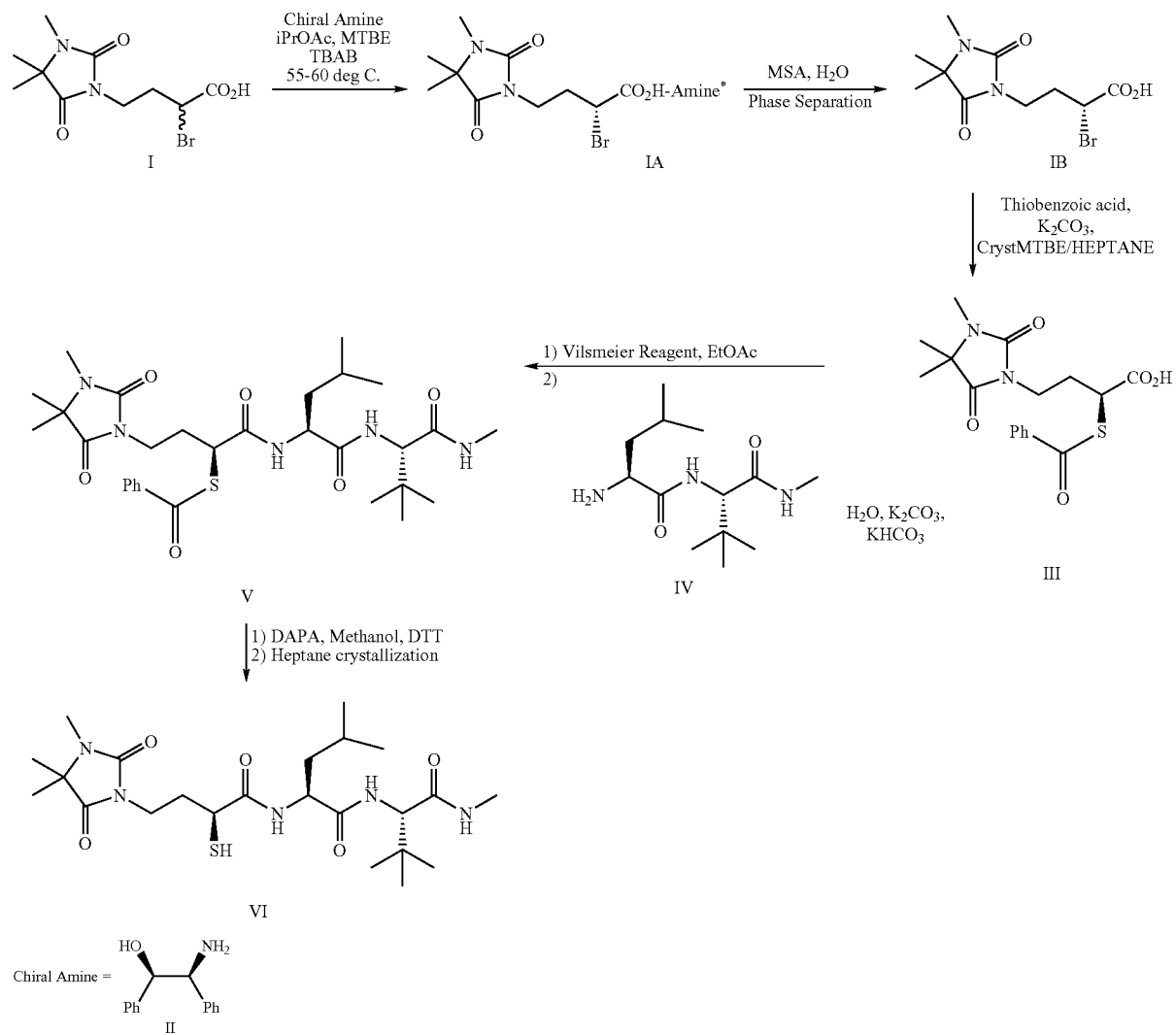

In one embodiment, the invention provides (a) 3,4,4-trimethyl-2,5-dioxo-1-imidazolidinebutanoic acid alpha-substituted with a leaving group (either R ★ or S ★ isomer, see definition below of R ★ and S ★), (b) (R)-α-Bromo-3,4,4-trimethyl-2,5-dioxo-1-imidazolidinebutanoic acid, or (c) a salt of one of the foregoing, in at least 88% ee. Alpha substitutions are preferably from chlorides, bromides, iodides, alkanoates, benzoates, thioalkanoates, thiobenzoates, thiolates, silyl alcoholates, and azides, particularly chlorides, bromides, iodides and azides.

In one embodiment, the invention provides (S)-α-(Benzoylthio)-3,4,4-trimethyl-2,5-dioxo-1-imidazolidinebutanoic acid, or a salt thereof, in at least 99% ee.

Other agents whose preparation relies on an α-substituted carboxylic acid as an intermediate are vasopeptidase inhibitors, such as Omapatrilat {otherwise known as [4S-[4α(R*),7α,10aβ]]-octahydro-4-[(2-mercapto-1-oxo-3-phenylpropyl)amino]-5-oxo-7H-pyrido[2,1-b] [1,3]thiazepine-7-carboxylic acid} and Gemopatrilat {otherwise known as [(S)-(R*, R*)]-hexahydro-6-[(2-mercapto-1-oxo-3-phenylpropyl)amino]-2,2-dimethyl-7-oxo-1H-azepine-1-acetic acid}. In this synthesis of this inhibitor, and in the synthesis of other related vasopeptidase inhibitors, chiral non-racemic α-substituted 3-phenylpropanoic acids, which are α-substituted with a leaving group serve as useful synthetic intermediates. Specifically, in the synthesis of Omapatrilat, (2R)-2-bromo-3-phenylpropanoic acid (VIIR) serves as a preferred synthetic intermediate. (As used in this application, 2-bromo-3-phenylpropanoic acid refers to 2-bromo-3-benzenepropanoic acid, 2-bromo-3-phenylpropionic acid, or α-bromo-3-phenylpropanoic acid). (2R)-2-bromo-3-phenylpropanoic acid (VIIR) is the precursor to (2S)-2-acetylthio-3-phenylpropanoic acid (VIII). (2R)-2-Bromo-3-phenylpropanoic acid (VIIR) is derived from D-phenylalanine (IXR) via a diazotization-bromination reaction. See, WO 9942431, U.S. Pat No. 5,366,272, EP 657453, and EP 629627. The cost of D-phenylalanine (IXR), which has the opposite stereochemistry form the corresponding natural product, is high and its availability may be limited. Enzymatic resolution methods for generation of (2R)-2-bromo-3-phenylpropanoic acid (VIIR) and optically active 2-acetylthio-3-phenylpropanoic acid (VIII) have also been reported. See JP 10014590, JP 96188811, and JP P2000-23693A. However, the costs associated with the reported processes are relatively high.

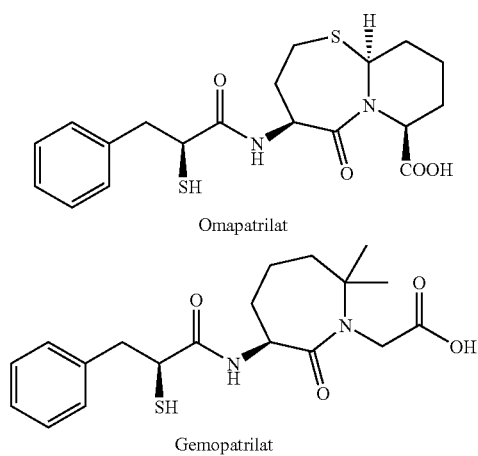

Omapatrilat

Gemopatrilat

In contrast, enantiomerically enriched or enantiomerically pure VIIR can be conveniently prepared from inexpensive L-phenylalanine (IXS) using the method of the present invention. Overall, the transformation of L-phenylalanine into (2S)-2-acetylthio-3-phenylpropanoic acid (VIII) is shown in Scheme 3.

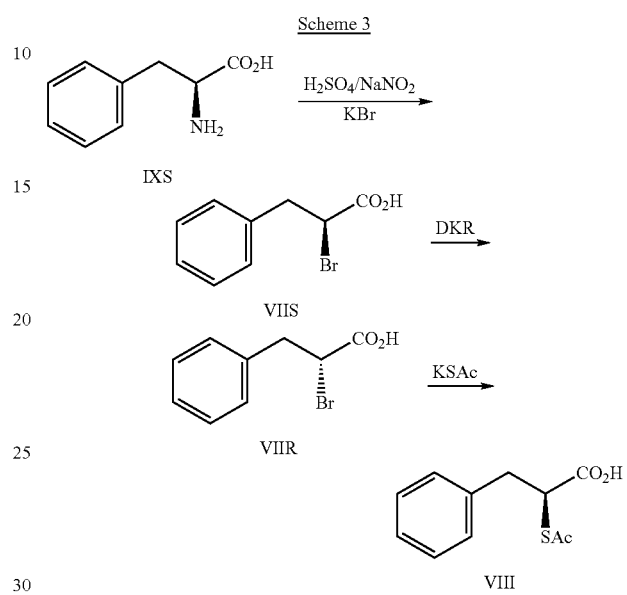

L-phenylalanine (IXS) is converted to (2S)-2-bromo-3-phenylpropanoic acid (VIIS). VIIS is then subjected to dynamic kinetic resolution conditions (DKR). This process yields the corresponding enantiomer, (2R)-2-bromo-phenylpropanoic acid (VIIR). The process, together with recycling aspects, is further illustrated in Scheme 4, below. (2S)-2-Bromo-phenylpropanoic acid VIIS is racemized by a nucleophile (bromide) in situ. (R)-Bornylamine (X) is used as the homochiral amine. Through dynamic kinetic resolution, the bornylamine salt of (2R)-2-bromo-3-phenylpropanoic acid (VI-IRB) is formed with high stereospecificity and with good yield. The bromo acid (VIIR) is then separated from the amine, and is subsequently converted to (2S)-2-acetylthio-3-phenylpropanoic acid (VIII). Thus, one embodiment of the invention provides for a method of inverting the configuration of an α-center of one enantiomer to obtain the other desired, enantiomer. The undesired enantiomer may be more readily available or cheaper than the desired enantiomer. Through the resolution method of the present invention then, these advantages are passed on to the desired enantiomer.

It can be recognized that the dynamic kinetic resolution method could readily be practiced to prepare alpha substituted 3-phenyl substituted carboxylic acids that are further substituted on the phenyl group. These phenyl substituents can, for example, include mono substitutions at the ortho, meta, or para positions. Additionally, these phenyl substitutions can, for example, include $C_1$-$C_6$ (preferably $C_1$-$C_3$) alkyl, $C_1$-$C_6$ (preferably $C_1$-$C_3$) alkoxy, cyano, nitro, halo (including fluoro, chloro, bromo, or iodo) and trifluoromethyl substituents. Preferably there are three or fewer phenyl substitutions.

One embodiment of the invention also provides for the isolation of (2R)-2-bromo-3-phenylpropanoic acid (VIIR) from racemic 2-bromo-3-phenylpropanoic acid (VII) using R-bornylamine. (Racemic VII can be prepared by treating racemic phenylalanine with sodium nitrite in the presence of acidic KBr.) Similarly, (2S)-2-bromo-3-phenylpropanoic acid (VIIS) isomer can be isolated using dehydroabietylamine (Aldrich, Milwaukee, Wis.) from racemic VII in the dynamic kinetic resolution of the invention as well.

In one embodiment, the invention provides (a) 3-phenylpropanoic acid alpha-substituted with a leaving group (either R★ or S★ isomer, see definition below of R★ and S★), (b) (2R)-2-bromo-3-phenylpropanoic acid, or (c) a salt of one of the foregoing. Alpha substitutions are preferably from chlorides, bromides, iodides, alkanoates, benzoates, thioalkanoates, thiobenzoates, thiolates, silyl alcoholates, and azides, particularly chlorides, bromides, iodides and azides.

encoded by the genetic code and norleucine, norvaline, ornithine, penicillamine (β-mercapto valine), ethionine, α-amino adipic acid, α-amino butyric acid, and the like. As illustrated above, a typical sequence of steps that can produce the R-enantiomer of the alpha-substituted carboxylic acid involves diazotizing the (αL)-amino acid with a nitrite salt and an appropriate anion salt (nucleophile) under acidic conditions, conducting the dynamic kinetic resolution, and isolating the R-enantiomer of the alpha-substituted carboxylic acid. Appropriate anion salts include chlorides, bromides, iodides, alkanoates, benzoates, thioalkanoates, thiobenzoates, thiolates, silyl alcoholates, and azides, particularly chlorides, bromides, iodides and azides. As the resulting

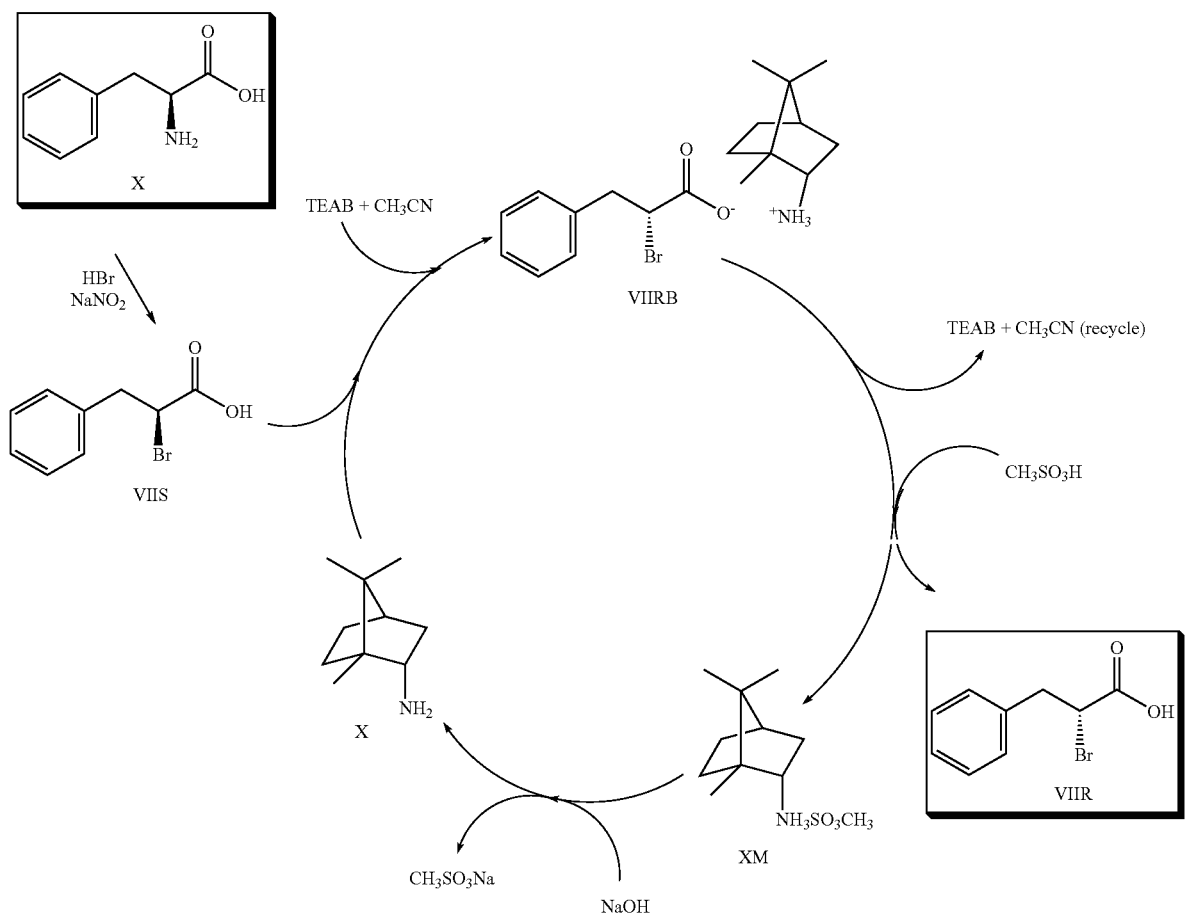

Scheme 4

TEAB = etraethylammonium bromide

More generally it can be recognized that the invention provides a method utilizing a bulk sourced amino acid (such as an (αL)-amino acid) to produce the desired enantiomer of an alpha-substituted carboxylic acid, wherein the alpha substitution is by chlorides, bromides, iodides, alkanoates, benzoates, thioalkanoates, thiobenzoates, thiolates, silyl alcoholates, azides, and the like, and the alpha carbon is chiral. The desired enantiomer of the alpha substituted carboxylic acid can have the opposite configuration of the starting amino acid. Bulk sourced amino acids are any amino acids that are available from a natural product or are readily synthesized. These include, for example, the amino acids product of the above sequence can contain an alpha leaving group, the product of this sequence can serve as a useful enantiomerically enriched or enantiomerically pure intermediate. A preferred embodiment of the invention provides a method of utilizing bulk-sourced aromatic-ring containing alpha amino acids, for example, phenylalanine, tyrosine, tryptophan, and histidine, for the preparation of chiral, nonracemic alpha-substituted carboxylic acids, wherein the alpha substitution is as described above.

It can be recognized that appropriate protecting groups may be necessary to protect reactive functional groups that are components of the side chains in order to efficiently effect the above described processes. For example, appropriate protection/deprotection schemes are necessary for the thiol, hydroxyl, carboxylic acid, and amino groups in cysteine, serine, glutamic acid, and lysine, respectively. Protecting groups for these functional groups are well known to those skilled in the art of organic synthesis, and are widely commercially available. For thiol groups, such protecting groups include, for example; thioesters, including thiobenzoates and $C_1$-$C_6$ thioalkanoates; and thiocarbamates.

In one embodiment, the invention provides (a) 3-phenylpropanoic acid alpha-substituted with a leaving group (either R★ or S★ isomer), (b) (2R)-2-bromo-3-phenylpropanoic acid, or (c) (2S)-2-bromo-3-phenylpropanoic acid, (d) a salt of one of the foregoing, in at least 95% ee. Substitutions are, for example, from chlorides, bromides, iodides, alkanoates, benzoates, thioalkanoates, thiobenzoates, thiolates, silyl alcoholates, and azides, particularly chlorides, bromides, iodides, azides, and the like.

In one embodiment, the invention provides a diastereomeric salt of (2S)-2-thioacetyl-3-phenylpropanoic acid with a chiral amine, preferably in at least 98% ee.

The invention further provides isomerically enriched products prepared by the method of the invention. Such compounds include those prepared in 80, 88, 90, 95, 98 or 99% ee.

DEFINITIONS

The following terms shall have, for the purposes of this application, the respective meaning set forth below.

The phrase "conditions selected to promote nucleophilic substitution of the anion and the leaving group" is not intended to indicate that $S_N2$ nucleophilic substitution necessarily occurs, but simply that appropriate reaction conditions are believed to be those promoting such nucleophilic substitution.

The R★ and S★ isomers are, with respect to compounds having a generally designated leaving group at the chiral carbon, the isomers that would be designated as R or S, respectively, if the leaving group were bromide.

The term "polymorph" refers to a solid crystalline phase of a given compound resulting from the possibility of at least two different arrangements of molecules of that compound in the solid state. Further, "polymorph" may be used interchangeably with "crystal form".

A "strong base" is one effective to promote enolization of a respective alpha-substituted carboxylic acid. In certain embodiments, such a strong base has a conjugate acid with pKa of at least 12, preferably at least 15.

The phrase "without substantial substitution of the leaving group with the amine of the chiral amine" means that no more than 0-2% or 0-5% of the alpha-substituted carboxylic acid is consumed in such a side reaction. Preferably, no more than 0.5% w/w% of the alpha-substituted carboxylic acid is so consumed.

The following examples further illustrate the present invention, but of course, should not be construed as in any way limiting its scope.

EXAMPLE 1

Preparation of (αS)-α-Mercapto-3,4,4-trimethyl-2,5-dioxo-1-imidazolidinebutanoyl-L-leucyl-N,3-dimethyl-L-valinamide (VI)

α-Bromo-3,4,4-trimethyl-2,5-dioxo-1-imidazolidinebutanoic acid (I) (111 g, 362.4 mmol) and (1R,2S)-(−)-2-amino-1,2-diphenylethanol (II) (the chiral amine, 75 g, 351 mmol, Aldrich) and tetrabutylammonium bromide (catalytic nucleophile, 2.4 g) were charged to a flask. I was obtained by/from Aerojet Fine Chemicals (a Division of Gencorp, Rancho Cordova, Calif.). To this was added 3 L of a 1:1 mixture of i-propyl acetate (i-PrOAc) and methyl t-butyl ether (MTBE). The resulting slurry was heated to 55-60° C. for 24 to 48 h. Reaction was deemed complete when the ratio of the diastereomers was ≧94:6 (R:S). The reaction was cooled to room temperature and the diastereomeric salt, (R)-α-bromo-3,4,4-trimethyl-2,5-dioxo-1-imidazolidinebutanoic acid, [R-(R*,S*)]-β-amino-α-phenylbenzeneethanol salt (1:1) (IA), was isolated by filtration. The product cake was washed with 850 mL of MTBE. The MTBE wet product cake was suspended in 1800 mL of MTBE. Water, 1800 mL was added. The pH of the aqueous phase was adjusted to between 1 and 2 with methanesulfonic acid (~23 mL). The phases were separated and the lower aqueous phase was extracted with MTBE (3×1L). The combined organic phases were washed with water (250 mL). The product, (R)-α-bromo-3,4,4-trimethyl-2,5-dioxo-1-imidazolidinebutanoic acid (IB) was used directly in the next step without isolation. In process yield and quality was 101.0 g, 93.0 M%, 87.4% ee (enantiomeric excess). IB: $^1$H NMR (CDCl$_3$): δ(ppm)= 4.30 (m, 1H), 3.72 (m, 2H), 2.96 (s, 3 H), 2.48 (m, 1H), 2.27 (m, 1H), 1.39 (s, 6H). $^{13}$C NMR (CDCl$_3$): δ (ppm)=176.7, 172.2, 155.2, 61.4, 41.7, 36.6, 33.2, 24.4, 21.9, 21.9. IR (KBr): ν (cm$^{-1}$)=3000 (br), 1740 (s), 1680 (s), 1450 (br), 1250 (s).

Chiral HPLC Analysis: IB

| | |
|---|---|
| Column | Chiralpak AD, 0.46 × 25 cm, 10 μ |
| Eluent | 40% (v/v) EtOH (absolute) in Hexane, 0.1% (v/v) TFA |
| Flow rate | 1.0 mL/min |
| Detection | 230 nm |
| Injection volume | 20.0 μL |
| Sample preparation | 5 mg in 10 mL ethanol (absolute) |
| Rt (min) = 10.0 (4.95 Area %), 12.0 (92.39 Area %). | |
| Retention times, min, | |
| Enantiomer of IB | 10.0 (S-Enantiomer of I) |
| IB | 12.0 (R-Enantiomer I) |

The MTBE solution of IB was concentrated and azeotropically dried to a concentration of 100 mg/mL (~1000 mL total volume). The dry solution was cooled to room temperature and contacted with powdered potassium carbonate (2.0 equivalents). Thiobenzoic acid (49.5 g, 348.0 mmol) was added to the reaction and the mixture was stirred at room temperature for 3-4 h. At the completion of the reaction, water (360 mL) was added to the mixture and the pH of the aqueous phase was adjusted to between 3.5 and 4.5 with glacial acetic acid (~42 g) in water (1:1). After stirring for 10-15 minutes, the layers were allowed to separate. The aqueous phase was extracted with 500 mL of MTBE. The combined organic phases were washed with water. Approximately 0.1% (v/v) of acetic acid was added to the mixture and the solution was concentrated to a volume of 880 mL. While maintaining a pot temperature of 50-55° C., heptane was slowly added and the solution was held at that temperature until crystallization became evident. The solution was cooled to room temperature for 1 to 2 hours and then further cooled to 0 to 5° C. for 1 to 2 hours. The product was isolated by filtration, washed with cold MTBE/heptane (1:1) and dried to constant weight. The product, (S)-α-(benzoylthio)-3,4,4-trimethyl-2,5-dioxo-1-imidazolidinebutanoic acid (III) was received as a white to off-white crystalline solid in 68 M% yield overall from I, 99.6% ee by chiral HPLC analysis. $^1$H NMR (CDCl$_3$): δ(ppm)=7.98 (d, 8.0 Hz, 2 H), 7.60 (t, 8 Hz, 1H), 7.48 (t, 8.0 Hz, 2H), 4.40 (m, 1H), 3.78 (m, 2H), 2.96 (s, 3 H), 2.42 (m, 1H), 2.10 (m, 1H), 1.47 (s, 3H), 1.43 (s, 3H). $^{13}$C NMR (CDCl$_3$): δ(ppm)= 189.6, 176.9, 172.7, 155.3, 135.9, 133.8, 128.6, 127.3, 61.4, 42.7, 36.5, 30.7, 24.4, 21.8, 21.7. IR (KBr): ν (cm$^{-1}$)=3000 (br), 1740 (s), 1680 (s), 1450 (br), 1220 (s), 1180 (s), 900 (s), 780 (s), 690 (s).

Chiral HPLC Analysis: III

| | |
|---|---|
| Column | Chiralpak AD, 0.46 × 25 cm, 10 μ |
| Eluent | 40% (v/v) EtOH (absolute) in Hexane, 0.1% (v/v) TFA |
| Flow rate | 1.0 mL/min |
| Detection | 230 nm |
| Injection volume | 20.0 μL |
| Sample preparation | 5 mg in 10 mL ethanol (absolute) |
| Rt (min) = 8.0 (0.20 Area %), 10.0 (99.80 Area %). | |
| Typical retention times, min, | |
| III | 8.0 (S-Enantiomer) |
| | 10.0 (R-Enantiomer) |

III (7.5 g, 20.6 mmol) was charged to a 250 mL round bottomed flask with a thermocouple and nitrogen inlet tube. Ethyl acetate (75 mL) was added to the flask and the mixture was agitated to produce a slurry. The flask was cooled to −22 to −25° C. Vilsmeier reagent (3.2 g, 25.0 mmol, 1.21 eq.) was charged to the slurry under a nitrogen blanket. The reaction was agitated until deemed complete by HPLC analysis (1-2 hours).

In a 500 mL round bottomed flask was charged L-leucyl-N,3-dimethyl-L-valinamide (IV) (dipeptide, 5.83 g, 22.64 mmol), potassium carbonate (0.57 g, 4.12 mmol) and potassium bicarbonate (10.31 g, 102.9 mmol). With stirring, 40 mL of deionized water was added and the mixture was agitated. The contents of the vessel were cooled to 0° C. and an acid chloride solution, prepared as described above, was added to the solution, controlling the rate of addition so as to maintain a pH range of 5.5 to 8.4. The reaction was agitated until deemed complete by HPLC analysis. The phases were separated. The product rich organic phase was treated with 1N HCl (~25 mL) to remove unreacted IV. The organic phase was washed with sodium bicarbonate solution (25 mL) to remove excess III and the phases were separated. The organic phase was washed with water to remove residual DMF. The product rich organic phase was concentrated at atmospheric pressure to azeotropically dry the solution (KF≦0.02%). The volume of the solution was adjusted to 150 mL. Heptane (50 mL) was slowly added to the reaction mixture at 70-80° C. The batch was cooled to 25-30° C. and the crystals were allowed to age for 4-5 hours. The product was filtered and the cake was washed with cold ethyl acetate/heptane (6:4). The wet cake was dried in a vacuum oven to a constant weight. (αS)-α-(Benzoylthio)-3,4,4-trimethyl-2,5-dioxo-1-imidazolidinebutanoyl-L-leucyl-N,3-dimethyl-L-valinamide (V) was received as a white to off-white crystalline solid, 10.21 g, 82.2% yield, HPLC area % 99.7%. $^1$H NMR (CDCl$_3$): δ(ppm)=7.89 (d, 7.5 Hz, 2 H), 7.60 (t, 7.4 Hz, 1H), 7.40-7.46 (t, 8.0 Hz, 3H), 7.23 (1H, d, 9.4 Hz); 6.35 (1H, br); 4.37-4.41 (m, 1H), 4.33 (1H, d, 9.4 Hz); 3.60-4.3 (m, 3H); 2.93 (s, 3 H); 2.75 (3H, d, 4.7 Hz); 1.5-2.5 (m, 5H); 1.47 (s, 3H), 1.46 (s, 3H); 0.99 (9H, s); 0.91 (6H, dd, 15.1 Hz). $^{13}$C NMR (CDCl$_3$): δ(ppm)=191.35; 177.62; 171.98; 170.69; 155.66; 136.19; 133.91; 128.73; 127.23; 61.56; 60.62; 53.43; 44.09; 40.89; 36.66; 34.68; 32.58; 25.70; 25.95; 24.81; 24.54; 23.06; 22.07; 21.77; 21.41. IR (KBr): ν (cm$^{-1}$)=3334 (br), 3298, 2955, 1757 (s), 1711, 1690, 1665, 1526, 1465, 1388, 1209, 912.

III has also been made by another synthetic route. III (62.87 g, 172.5 mmol) was charged to a 250 mL round bottomed flask equipped with a thermocouple, nitrogen inlet tube and addition funnel. Ethyl acetate (600 mL) was added to the flask and the mixture was agitated to produce a slurry. The flask was cooled to 0-5° C. Isobutyl chloroformate (24.00 g, 175.8 mmol, 1.02 eq.) was charged to the slurry under a blanket of nitrogen. A solution of N-methylmorpholine (NMM) in ethyl acetate (17.02 g, 168.3 mmol, 0.98 eq. in 110 mL of ethyl acetate) was slowly charged to the vessel, insuring that the internal reaction temperature remained +/−3° C.

A 1000 mL round bottomed flask was charged IV (dipeptide, 44.20 g, 171.7 mmol, 1.0 eq.), NMM (1.75 g, 17.3 mmol, 0.10 eq.) and ethyl acetate (500 mL). This solution was added in a single portion to the reaction vessel over a 3-4 minute period. A 10-12° C. exotherm is observed during this charge. The reaction was stirred until deemed complete by HPLC analysis of a reaction aliquot.

The reaction was quenched by the addition of deionized water (400 mL) to a vigorously stirred reaction mixture. The mixture was heated to 40-50° C. to prevent the product from precipitating from the organic phase. The phases were separated and the organic phase was washed with 400 mL of a 5% (w/v) solution of sodium carbonate in deionized water. The mixture was again heated to 40-50° C. and the phases were separated. The organic phase was finally washed with deionized water (400 mL), heated to 40-50° C. and the phases were separated. The organic phase was concentrated at atmospheric pressure to azeotropically dry the solution and adjust the final volume to 1200 mL. The reaction mixture was cooled to 20-25° C. and n-heptane (400 mL) was added to the batch over a 30 min period. The resulting slurry was held at 20-25° C. for 1-4 hours, and was filtered on a Buchner funnel. The solids were rinsed with a 40:60 mixture of ethyl acetate/n-heptane and the product was dried in vacuo to give the desired product, V, as a white to slightly pink colored crystalline solid, 95.89 g, 92.5% yield, 99.77% purity by HPLC area analysis. $^1$H NMR (CDCl$_3$): δ(ppm)= 7.89 (d, 7.5 Hz, 2 H), 7.60 (t, 7.4 Hz, 1H), 7.40-7.46 (t, 8.0 Hz, 3H), 7.23 (1H, d, 9.4 Hz); 6.35 (1H, br); 4.37-4.41 (m, 1H), 4.33 (1H, d, 9.4 Hz); 3.60-4.3 (m, 3H); 2.93 (s, 3 H); 2.75 (3H, d, 4.7 Hz); 1.5-2.5 (m, 5H); 1.47 (s, 3H), 1.46 (s, 3H); 0.99 (9H, s); 0.91 (6H, dd, 15.1 Hz). $^{13}$C NMR (CDCl$_3$): δ(ppm)=191.35; 177.62; 171.98; 170.69; 155.66; 136.19; 133.91; 128.73; 127.23; 61.56; 60.62; 53.43; 44.09; 40.89; 36.66; 34.68; 32.58; 25.70; 25.95; 24.81; 24.54; 23.06; 22.07; 21.77; 21.41. IR (KBr): ν (cm$^{-1}$)=3334 (br), 3298, 2955, 1757 (s), 1711, 1690, 1665, 1526, 1465, 1388, 1209, 912.

To a three-necked 500 mL flask equipped with mechanical stirrer, thermocouple, and heating mantle, was charged V (25 g, 41.4 mmole, 1 equiv.), and DTT (dithiothreitol, 160 mg, 0.025 equiv.) under N$_2$ atmosphere. Deoxygenated isopropyl acetate (99.8±10 mL) was charged to the flask. The resulting slurry was agitated. In a separate vessel, DAPA (3-dimethylaminopropylamine, 8.4 g, 2 equiv.) was dissolved in 25±5 mL methanol. The solution was degassed. The DAPA-methanol solution was added to the reaction vessel, maintaining the temperature in the range of 28±10° C. The reaction was stirred at approximately 28±10° C. until the reaction was judged to be complete by HPLC assay. The reaction was quenched by addition of 78 mL of deoxygenated aqueous 2M HCl and agitated for at least 10 min. The phases were allowed to separate. The upper organic solution was washed with 78 mL 1N HCl from Step 2, and agitated for at least 10 min. The phases were separated and the combined aqueous layers extracted with 45 ml of isopropyl acetate. The product rich organic phase was washed with 78 mL of water and agitated for at least 10 min. The batch was concentrated by atmospheric distillation until the KF of the distillate was <0.1 wt % water content, the final volume was 75 mL and the HPLC area percent ratio of (αS)-α-mercapto-3,4,4-trimethyl-2,5-dioxo-1-imidazolidinebutanoyl-L-leucyl-N,3-dimethyl-L-imidazolidinebutanoyl-L-leucyl-N, 3-dimethyl-L-valinamide (VI) to i-PrOAc is between 90:10 to 95:5. The distillate was cooled to ambient temperature and polish filtered. The filter pad was washed with i-PrOAc. The volume of the product rich isopropyl acetate solution was adjusted to 75 mL. The isopropyl acetate solution was heated to approximately 80±10° C. and the solution was seeded with crystals of VI (~25 mg). The slurry was held at 75±10° C. for 1 to 2 h. Heptane (~50 mL) was slowly added while maintaining a pot temperature of 75+5° C. This was held for 1-2 hours. The solution was cooled to ambient temperature and held for 1 to 2 hours. The product was isolated by filtration. The product cake was washed with 100 to 150 mL solution of 3:2 (v/v) deoxygenated heptane/isopropyl acetate until the area percent of (αR)-α-mercapto-3,4,4-trimethyl-2,5-dioxo-1-imidazolidinebutanoyl-L-leucyl-N,3-dimethyl-L-valinamide in the wash was less than 0.4% of the area percent of isopropyl acetate plus area percent of VI. The product was dried under vacuum at not more than 55° C. until the loss on drying was <1%. VI was obtained as a white crystalline solid, 18.2 g (88.0 M%), 99.8% area% by HPLC analysis. $^1$H NMR (500 MHz., CDCl$_3$): δ(ppm) 0.96 (3H, d, 7.0 Hz); 0.97 (9H, s); 0.98 (3H, d, 6.3 Hz); 1.40 (3H, s) 1.41 (3H, s); 1.64 (1H, m); 1.71 (1H, m); 1.73 (1H, m); 1.99 (1H, m); 2.24 (1H, m); 2.33 (1H, d, 10.1 Hz); 2.76 (3H, d, 4.8 Hz); 2.90 (3H, s); 3.30 (1H, dt, 5.0, 10.1 Hz); 3.56 (1H, m); 3.67 (1H, dt, 4.7, 14.6 Hz); 4.29 (1h, d, 9.6 Hz); 4.48 (1H,m); 6.28 (1H, bs); 7.09 (1H, d, 9.6); 7.29 (1H, d, 9.3 Hz). $^{13}$C NMR (125 MHz., CDCl$_3$): δ (ppm)=21.8; 22.0; 22.1; 23.0; 24.5; 24.9; 26.0; 26.6; 34.8; 36.7; 37.0; 40.5; 41.3; 53.1; 60.6; 61.4; 155.7; 170.6; 172.0; 172.1; 177.3. IR (KBr): ν (cm$^{-1}$)=3320 (s); 2955 (m); 1769 (m); 1707 (vs); 1643 (vs); 1539 (s); 1464 (s); 1385 (m); 1368 (m).

EXAMPLE 2

Screening Studies to Investigate Dynamic Resolutions

Screening techniques were used to identify unique combinations of chiral amines and solvents that would be capable of effecting a dynamic resolution on a particular substrate. Since a dynamic resolution requires a crystal slurry at elevated temperature, the screening study identified chiral amine/solvent combinations that form crystal slurries at 50° C. Racemic acids (25 μmol) were dispensed into a panel of HPLC vials, and a unique combination of chiral amine and solvent was added to each vial. The vials were incubated at 50° C. for 0.5 hours and then visually checked for the presence of salts. The vials were then judged according to the following table:

| Observation: | Description: |
|---|---|
| S | Solids; Vial contained large amounts of solid materials that were free flowing |
| T | Triturated Solids: Vial contained solids that clung to sides of the vessel |
| LS | Light Solids: Vial contained small quantities of solid material |
| O | Oil: Vial contained an oil |

The desired response was "S" which would theoretically afford sufficient yields and handling characteristics required for a process. The response of "T" would have potential for development if a better handling slurry could be obtained for scale up. A response of "LS", indicates material that may have potential for development if higher yielding, related solvent combination could be found. A response of "O" indicates an oil which would have low potential for further development, these samples were stored at low temperature (−10° C.) for 2 weeks in an attempt to induce solid formation. Vials that do not have any observation recorded indicate the sample remained in solution both at 50° C., and after incubating for a week at low temperature (−10° C.)

Screen Development:

Scheme 4

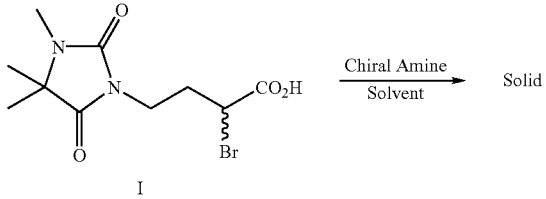

The initial chiral amine/solvent screen was performed on I (racemic bromo acid) using 4 readily available chiral amines in 10 solvents (see Table 1). The chiral amines were obtained from Aldrich. 1 M methylene chloride solutions of appropriate amines and bromo acid were dispensed into 40 HPLC vials. The solvent was removed using a vacuum centrifuge, and the desired test solvent was dispensed into the appropriate containers. Of the 40 solvent/amine combinations, R-methylbenzylamine was the most effective.

TABLE 1

Results of initial screen

| Row | Amine | Solvent | | | | | | | | | | % R Br Acid |
|---|---|---|---|---|---|---|---|---|---|---|---|---|
| | | 1 | 2 | 3 | 4 | 5 | 6 | 7 | 8 | 9 | 10 | |
| 1 | (1R,2S)-(+)-cis-1-Amino-2-indanol | | | | | | | | | | | |
| 2 | (−)-Sparteine | S | | S | T | | | O | T | T | | impurity |

TABLE 1-continued

Results of initial screen

| Row | Amine | Solvent 1 | 2 | 3 | 4 | 5 | 6 | 7 | 8 | 9 | 10 | % R Br Acid |
|---|---|---|---|---|---|---|---|---|---|---|---|---|
| 3 | (R)-(+)-α-Methylbenzylamine | S | | S | | | | T | | | | 46-49 |
| 4 | Dehydroabeitylamine | | | | | | | | | | | |

Solvents: 1 = THF, 2 = Acetone, 3 = Ethyl Acetate, 4 = Butyl Acetate, 4 = n-Butanol, 6 = Acetonitrile, 7 = MTBE, 8 = MIBK, 9 = Isopropyl Acetate, 10 = Water Early Optimization: A total of 37 optimization experiments in reactor blocks were performed to develop the dynamic resolution with S-Methyl benzylamine. These studies were optimized to afford an 85% yield of salts containing an 80:20 ratio of desired to undesired enantiomer of I, with ee analyzed by chiral HPLC.

Full Screen: The full screen of racemic I was performed with 43 additional chiral amines (Aldrich) and seven solvents. This screen identified 3 additional amines, (S)-(−)-α,α-diphenyl-2-pyrrolidinemethanol, (1R,2S)-(−)-ephedrine, and (1S,2R)-(+)-2-amino-1,2-diphenylethanol, that afforded solids when heated at 50° C. Table 2 shows the results:

TABLE 2

Results from the Full Screen of α-Bromo-3,4,4-trimethyl-2,5-dioxo-1-imidazolidinebutanoic acid:

| Vial | Amine | EtOAc | BuOAc | BuOH | CH3CN | MTBE | MIBK | % R Br Acid |
|---|---|---|---|---|---|---|---|---|
| 1 | S-(−)-Methioninol | | LS | LS | | | | |
| 2 | S-(+)-2-(Aminomethyl)pyrrolidine | O | O | O | | O | O | |
| 3 | (S)-(−)-1-Benzyl-2-pyrrolidinemethanol | | | | | O | | |
| 4 | (S)-(+)-Leucinol | | | | | O | | |
| 5 | (S)-(−)-2-Methylbutyl amine | | | | | | | |
| 6 | (R)-(−)-2-Amino-1-butanol | | | | | | | |
| 7 | (S)-(−)-1-Benzyl-3-pyrrolidinol | | | | | O | | |
| 8 | (S)-(+)-Isoleucinol | | | | | O | | |
| 9 | (R)-(−)-1-Amino-2 propanol | | O | | | O | | |
| 10 | (R)-(−)-2-Amino-1-propanol | | | | | O | | |
| 11 | (R)-(−)-1-Cyclohexylethylamine | | | | | | | |
| 12 | (S)-(+)-2-Amino-3-methyl-1-butanol | | | | | | | |
| 13 | (S)-(−)-N,N-Dimethyl-1-phenethyl amine | | T | | | O | | |
| 14 | (S)-(+)-sec-Butylamine | | | | | | | |
| 15 | (S)-(−)-Nicotine | | | | | O | | |
| 16 | (S)-(+)-2-Pyrrolidinemethanol | | | | | O | | |
| 17 | (S)-(−)-α-Methyl-4-pyridinemethanol | | | | | O | | |
| 18 | (−)-cis-Myrtanylamine | | | | | | | |
| 19 | Chirald ® | | | | | O | | |
| 20 | S-Benzyl-L-cysteinol | | | | | O | | |
| 21 | (S)-(−)-2-Phenylglycinol | | O | | | | | |
| 22 | (S)-(−)-2-Amino-3-phenyl-1-propanol | | | | | | | |
| 23 | [(5R,11R)-(+)-2,8-dimethyl-6H,12H,-5,11-methano-dibnze[b,f][1,5]diazocine] | | | | | | | |
| 24 | (1S,2S)-(+)-N-Methylpseudoephedrine | | | | | O | | |
| 25 | (S)-(−)-α,αDiphenyl-2-pyrrolidinemethanol | S | S | S | | S | S | 50.5 |
| 26 | (4S,5S)-(−)-2-Methyl-5-phenyl-2-oxazoline-4-methanol | | | | | O | | |
| 27 | (1R,2S)-(−)-N-Methylephedrine | | | | | O | | |
| 28 | (1S,2S)-(+)-2-Amino-1-(4-nitrophenyl)-1,3-propanediol | LC | T | | | T | | — |
| 29 | (1S,2S)-(+)-Thiomicamine | | O | | | O | | |
| 30 | (1R,2S)-(−)-Norephedrine | | | | | O | | |
| 31 | L-α-Amino-ε-caprolactam | O | O | | LO | O | O | |
| 32 | R-(+)-Bornylamine | | | | | | | |
| 33 | (1S,2S)-(+)-2-Amino-3-methoxy-1-phenyl-1-propanol | | | | | O | | |
| 34 | (1S,2R)-(+)-2-Amino-1,2-diphenylethanol | | S | | | T | S | 42.9 |
| 35 | (1S,2S)-(+)-2-amino-1-phenyl-1,2-propanediol | | O | | | O | | |
| 36 | (R)-(−)-Isoproterenol | O | O/T | | | O/T | O | |
| 37 | (1S,2S)-(+)-Pseudoephedrine | | | | | O | | |
| 38 | (R)-(+)-1,1'-Binaphthyl-2,2'-diamine | | LS | | | | | — |
| 39 | (1R,2S)-(−)-Ephedrine | S | S | S | S | S | S | 49.6 |
| 40 | (1S,2S)-(+)-1,2-Diaminocyclohexane | | O | | | O | | |
| 41 | (1S,2S)-(−)-1,2-Diphenylethylenediamine | | | | | | | |
| 42 | (R)-(+)-α-Amino-γ-butyrolactone hydrochloride | | | | | | | |

TABLE 2-continued

Results from the Full Screen of α-Bromo-3,4,4-trimethyl-2,5-dioxo-1-imidazolidinebutanoic acid:

| Vial | Amine | EtOAc | BuOAc | BuOH | CH3CN | MTBE | MIBK | % R Br Acid |
|---|---|---|---|---|---|---|---|---|
| 43 | (S)-(+)-2-Amino-3-cyclohexyl-1-propanol hydrochloride | | | | | O | | |
| 44 | (R)-(−)-Phenylephrine hydrochloride | | | | | | | |

Each of these amines was tested for dynamic resolution. The most effective amine in resolving I was (1S,2R)-(+)-2-Amino-1,2-diphenylethanol, which afforded a salt containing a 93:7 ratio of the enantiomers (favoring the undesired enantiomer). Using the opposite enantiomer of the amine, the correct enantiomer (IA) was prepared in a 93:7 R:S enantiomer ratio.

EXAMPLE 3

Screen of 2-Bromo-3-phenylpropanoic acid (VII)

Scheme 5

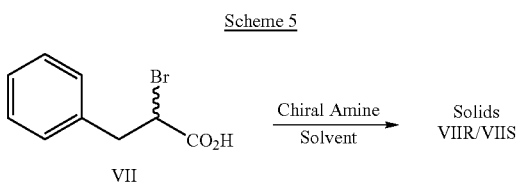

This dynamic resolution was investigated by screening racemic 2-bromo-3-phenylpropanoic acid against a panel of 49 chiral amines and 7 solvents to identify the chiral amine/solvent combinations that afford a crystal slurry at elevated temperatures. The promising chiral amine/solvent combinations were then subjected to dynamic resolution conditions for 16 hours and the resulting solids were analyzed for ee by chiral hplc. The products that afforded >90% ee were repeated to produce analytical samples and reported.

Screening Studies:

The chiral amines were prepared into 0.5 to 1.0 M solutions or slurries in dichloromethane. The racemic bromoacid (Racemic bromo acid was prepared by treating racemic phenylalanine with sodium nitrite in the presence of acidic KBr.) was diluted as a 1.0 M solution in dichloromethane. Approximately 20 μmols of racemic bromo acid was dispensed into 343 HPLC vials. Approximately 20 μmol of each chiral amines was dispensed into seven of the HPLC vials. The solvent was removed using a Savant Speed Vac, and 200 μL of the test solvent was dispensed into the appropriate vials such that each chiral amine was incubated with seven different solvents. The vials were incubated to 50° C. for 0.5 h on a J-KEM shaker heat block. The results of the screening studies are shown in Table 3. Representative vials from each chiral amine that afforded crystalline product were isolated on a centrifuge filter and analyzed for ee by chiral HPLC (Table 4).

TABLE 3

Results from the Full Screen of Chiral amines and Solvents with Racemic 2-Bromo-3-phenylpropanoic acid:

| # | Amine | THF | EtOAc | BuOAc | BuOH | CH3CN | MTBE | MIBK | Enan. Ratio |
|---|---|---|---|---|---|---|---|---|---|
| 1 | S-(−)-Methioninol | | | | | | O | | |
| 2 | S-(+)-2-(Aminomethyl)pyrrolidine | O | O | O | | O | O | O | |
| 3 | (S)-(−)-1-Benzyl-2-pyrrolidinemethanol | | | | | | | | |
| 4 | (S)-(+)-Leucinol | | | | | | | | |
| 5 | (S)-(−)-2-Methylbutyl amine | | | | | | | | |
| 6 | (R)-(−)-2-Amino-1-butanol | | | | | | O | | |
| 7 | (S)-(−)-1-Benzyl-3-pyrrolidinol | | | | O | | O | | |
| 8 | (S)-(+)-Isoleucinol | | | | | | | | |
| 9 | (R)-(−)-1-Amino-2 propanol | | | | | | O | | |
| 10 | (R)-(−)-2-Amino-1-propanol | | | | | | O | | |
| 11 | (R)-(−)-1-Cyclohexylethylamine | | | | | S | O | | +30 |
| 12 | (S)-(+)-2-Amino-3-methyl-1-butanol | | | | | | | | |
| 13 | (S)-(−)-N,N-Dimethyl-1-phenethylamine | | | | | | T | | |
| 14 | (S)-(+)-sec-Butylamine | | | | | | | | |
| 15 | (S)-(−)-Nicotine | | | T | | | O | | |
| 16 | (S)-(+)-2-Pyrrolidinemethanol | O | O | O | | | O | O | |
| 17 | (S)-(−)-α-Methyl-4-pyridinemethanol | O | O | O | | | O | | |
| 18 | (−)-cis-Myrtanylamine | | S | S | | S | S | OIL | −41 |
| 19 | (2S,3R)-(+)-4-dimethylamino-1,2-diphenyl-3-methyl-2-butanol | | LS | LS | LS | LS | LS | | +5 |
| 20 | S-Benzyl-L-cysteinol | | S | | | S | S | S | −31 |
| 21 | (S)-(−)-2-Phenylglycinol | | | | | | T | | |
| 22 | (S)-(−)-2-Amino-3-phenyl-1-propanol | | | | | | | | |
| 23 | [(5R,11R)-(+)-2,8-dimethyl-6H,12H,-5,11-methano-dibnzo[b,f][1,5]diazocine] | | | | | | | | |
| 24 | (1S,2S)-(+)-N-Methylpseudoephedrine | | | | | | O | | |
| 25 | (S)-(−)-α,αDiphenyl-2-pyrrolidinemethanol | S | S | S | | S | S | S | −20 |

TABLE 3-continued

Results from the Full Screen of Chiral amines and Solvents with Racemic 2-Bromo-3-phenylpropanoic acid:

| # | Amine | THF | EtOAc | BuOAc | BuOH | CH3CN | MTBE | MIBK | Enan. Ratio |
|---|---|---|---|---|---|---|---|---|---|
| 26 | (4S,5S)-(−)-2-Methyl-5-phenyl-2-oxazoline-4-methanol | | | | | | O | | |
| 27 | (1R,2S)-(−)-N-Methylephedrine | | | | | | O | | |
| 28 | (1S,2S)-(+)-2-Amino-1-(4-nitrophenyl)-1,3-propanediol | | LS | LS | LS | LS | | | |
| 29 | (1S,2S)-(+)-Thiomicamine | | | | | | O | | |
| 30 | (1R,2S)-(−)-Norephedrine | | | | | | | | |
| 31 | L-α-Amino-ε-caprolactam | | O | O | | S | O | | |
| 32 | R-(+)-Bornylamine | S | S | S | S | S | S | S | +8 |
| 33 | (1S,2S)-(+)-2-Amino-3-methoxy-1-phenyl-1-propanol | | | | | | | | |
| 34 | (1S,2R)-(+)-2-Amino-1,2-diphenylethanol | | | S | | | S | | +66 |
| 35 | (1S,2S)-(+)-2-Amino-1-phenyl-1,2-propanediol | | | | | | O | | |
| 36 | (R)-(−)-Isoproterenol | | T | T | | | T | | |
| 37 | (1S,2S)-(+)-Pseudoephedrine | | LS | | | | S | | +17 |
| 38 | (R)-(+)-1,1'-Binaphthyl-2,2'-diamine | | | | S | | T | | +5 |
| 39 | (1R,2S)-(−)-Ephedrine | S | S | S | S | S | S | S | +5 |
| 40 | (1S,2S)-(+)-1,2-Diaminocyclohexane | | | | | | O | | |
| 41 | (1S,2S)-(−)-1,2-Diphenylethylenediamine | | | | | | | | |
| 42 | (R)-(+)-α-Amino-γ-butyrolactone hydrochloride | | | | | | | | |

TABLE 4

EE Values of Isolated Salts from the Chiral Amine vs. Solvent Screen.

| Chiral Amine | Solvent | Salt e.e. |
|---|---|---|
| S-(+)-1-Cyclohexylethylamine | Acetonitrile | +30 |
| (−)-cis-Myrtanylamine | MTBE | −41 |
| (2S,3R)-(+)-4-dimethylamino-1,2-diphenyl-3-methyl-2-butanol | MTBE | +5 |
| S-Benzyl-L-cystienol | Acetonitrile | −31 |
| S-(−)-α,α-Diphenyl-2-pyrrolidinemethanol | Butyl acetate | −20 |
| L-α-Amino-ε-caprolactam | MTBE | +8 |
| R-(+)-Bornylamine | Butyl acetate | +41 |
| (1S,2R)-(+)-2-Amino-1,2-diphenylethanol | Butyl acetate | 66 |
| (1R,2R,3R,5S)-(−)-Isopinocamphylamine | MTBE | +1 |
| (1S,2S)-(+)-pseudoephedrine | MTBE | +17 |
| S-(−)-1-1'-Binaphyl-2,2'diamine | Butanol | +5 |
| (1R,2S)-(−)-Ephedrine | Ethyl acetate | +5 |
| (1R,2S)-(+)-cis-1-Amino-2-indanol | Butyl acetate | −5 |
| (−)-Sparteine | Ethyl acetate | −3 |
| Dehydroabietylamine | Butyl acetate | −13 |
| S-(+)-α-(methoxymethyl)phenethylamine•HCl | MTBE | +13 |

Dynamic Resolution Screen:

The chiral amines that afforded ee>±10 were then evaluated in a second study in which the dynamic resolution was attempted on a slightly larger scale (0.15-0.35 mmol). Chiral amine (0.9 eq.) and racemic bromo acid were incubated in the appropriate solvent (0.17 M) in the presence of tetrabutyl ammonium bromide (10 mg) for 16 h at 50° C. Samples were taken to determine the extent of conversion in the systems that afforded significant amounts of precipitation. (See Table 5)

TABLE 5

Dynamic Resolution Results for Chiral Amines from Screening Study

| Chiral Amine | Solvent | e.e. of salt | e.e. of dynamic resolution |
|---|---|---|---|
| S-(+)-1-Cyclohexylethylamine | Acetonitrile | 30 | Light slurry |
| (−)-cis-Myrtanylamine | MTBE | −41 | Decomposition |
| S-Benzyl-L-cystienol | Acetonitrile | −31 | Solution |
| S-(−)-α,α-Diphenyl-2-pyrroli-dinemethanol | Butyl acetate | −20 | −36 |
| R-(+)-Bornylamine | Butyl acetate | 41 | 90 |
| (1S,2R)-(+)-2-Amino-1,2-diphenylethanol | Butyl acetate | 66 | Solution |
| (1S,2S)-(+)-pseudoephedrine | MTBE | 17 | Light slurry |
| Dehydroabietylamine | Butyl acetate | −13 | −92 |
| (−)-Cinchonidine | Toluene | | 75 |

EXAMPLE 4

Repeat of Successful Dynamic Resolutions (2R)-2-Bromo-3-phenylpropanoic acid, bornyl amine salt (VIIRB):

To 60.2 mg of R-(+)-Bornylamine, 0.105 mL of racemic 2-bromo-3-phenylpropionic acid (VII), 5 mg of tetrabutyl ammonium bromide and 2 mL of butyl acetate were added to a 5 mL reaction tube. The samples were heated to 55° C., for 16 h, and the reaction was cooled to 20° C. The reaction mixture was filtered, washed with MTBE (2 mL), and dried to afford 100 mg (74%, 94.2% desired enantiomer) of VIIRB.

White solid, IR: KBr 1634, 1526, 1393. $^1$H NMR (DMSO-d6) δ 0.87 (s, 6H), 0.91 (s,3H), 1.08 (m, 2H) 1.35 (m, 1H), 1.61 (m, 2H), 2.21 (m, 2H), 2.78 (m, 1H), 3.22 (αβm, 2H), 4.32 (αβ, 1H), 7.28 (s, 5H). Elemental analysis: Theory 59.69% C; 7.38% H, 3.66% N, 20.90% Br; Found 59.49% C, 7.41% H, 3.63% N, 21.21% Br.

(2S)-2-Bromo-3-phenylpropanoic acid Dehydroabeitylamine salt (VIISD):

Dehydroabeityl amine (82.2 mg), 0.046 mL of racemic 2-bromo-3-phenylpropanoic acid (VII), 5 mg of tetrabutyl ammonium bromide and 2 ml of butyl acetate were added to a 5 mL reaction tube. The samples were heated to 55° C., for 16 h, and the reaction was cooled to 20° C. The reaction mixture was filtered, washed with MTBE (2 mL), and dried to afford 50 mg (57%, 88.2% desired enantiomer) of VIISD.

White solid, IR: KBr 1608, 1558, 1378, 702. $^1$H NMR (DMSO-d6) δ 0.82 (m, 3H), 0.98 (s, 3H), 1.24 (d, 6H), 1.37 (m, 2H), 1.52 (m, 1H), 1.58 (m, 2H), 1.63 (m, 3H), 2.42 (m, 2H), 2.78 (m, 2H), 3.28 (αβq, 2H), 3.78 (m, 1H), 4.37 (m, 1H), 6.85 (s, 1H), 6.98 (d, 1H), 7.08 (s, 1H), 7.18 (m, 5H). Elemental analysis: Theory 67.69% C; 7.84% H, 2.72% N, 15.53% Br; Found 67.65% C, 8.02% H, 2.81% N, 15.28% Br.

| HPLC Conditions: | |
|---|---|
| Mobile Phase: | 97% Hexane |
| | 3% Absolute Ethanol |
| | plus 0.1% Trifluoroacetic acid |
| Instrument: | Hewlett Packard 1090 |
| Column: | Chiralcel AD, 250 mm × 4.6 mm |
| Temperature: | ambient |
| Flow Rate: | 2 ml/min |
| Detector: | Diode array 220 nm |
| Retention time: | R-Enantiomer 5.3 min. |
| | S-Enantiomer 6.4 min. |

EXAMPLE 5

Preparation of (2S)-2-Bromo-3-phenylpropanoic acid (VIIS) from L-phenylalanine (IXS)

In a 1 L jacketed reactor equipped with mechanical stirring and thermometer, 48% HBr (408.2 g, 2.42 mol), water (150 mL) and toluene (168 mL) were charged at 15° C. under nitrogen flow. The mixture temperature was brought to 0° C. and L-phenylalanine (100 g, 0.605 moles) was added. The mixture was cooled to −5° C. A solution of sodium nitrite (54.3 g, 0.787 mol) in water (102 mL) was added dropwise to the reaction mixture over 2 hours. After the addition, the reaction mixture was stirred for 3 hours, and then the temperature was brought to 15° C., and stirring was maintained for another hour. The mixture was then left to stand for 30 minutes, and the phases separated. The organic layer was diluted with 260 mL toluene, and first washed with water (twice, 150 mL each), then with brine (150 mL). The organic phase was then separated and dried over MgSO$_4$. After removal of solvent, a total of 126.5 g of VIIS was obtained. The product was 90.0% pure (including 5 M% toluene) and had 94.7% ee. The yield was 88.9% after correction for toluene.

EXAMPLE 6

Preparation of (2R)-2-Bromo-3-phenylpropanoic Acid (VIIR) from Racemic 2-Bromo-3-phenylpropanoic Acid (VII) through Dynamic Kinetic Resolution Screening Studies Racemic 2-bromo-3-phenylpropanoic acid (VII) was subjected to dynamic kinetic resolution processes under different conditions. Various combinations of chiral amines, solvents and catalysts were used. A shaker system equipped with a 70-well heating block was employed. Initial testing of the system indicated that reaction done in this system gave similar results as the one ran in a flask equipped with a stir bar. Three series of reactions (Table 6, A1 to A7, B 1 to B4, C1 to C6) were then performed using the system. In reactions A1 to A7, the effects of different phasetransfer catalysts were studied on dynamic kinetic resolution of 2-bromo-3-phenylpropanoic acid (VII) via bornylamine (X). In reactions B1 to B4, a different chiral amine, (1S,2R)-2-amino-1,2-diphenylethanol, was used. Combinations of solvents were tested on this series. In reactions C1-C6, the effects of different solvents were studied using (R)-bornylamine (X) as chiral amine. The reactions were run according to the following procedure: Racemic bromo acid (0.050 mL, 0.319 mmol) was charged to 0.196 mmol of chiral amine in 4 mL vials. Tetrabutylammonium bromide or other phase transfer catalysts (PTC) (5 mg) and 1 mL of solvent were then added. The samples were sealed and heated to 55° C. in the rotating heating block (350 rpm) for 24 hrs or 48 hrs, then cooled to RT, filtered, washed with 2 mL MTBE. After drying, the bromo acid-amine salts were weighed for yields. To determine the ee of the bromoacid, 3 mg of each of the salts were suspended in mixtures of 2 mL pH 1.5 aqueous methanesulfonic acid/2 mL MTBE. After stirring for 5 min, the clear organic layers were washed with water and dried over MgSO$_4$. Chiral HPLC analysis of the organic layers were then performed. (Column: Chiralpak AD 250×4.6 mm; Column temperature; ambient; Mobile Phase: 97.9% of hexane, 2% of absolute ethanol and 0.1% TFA; The flow rate was 1.0 ml/minute and UV detection was at 215 nm).

The results are summarized in Table 6. Since reaction C-1, in which acetonitrile was used as solvent, gave the best ee (93.5%), the reaction was scaled up (about ×4 scale) in a flask. Two reactions (ACN-1, ACN-2) were run under the same conditions, with reaction 1 stopped at 24 hr, and reaction 2 stopped at 48 hr. The results were summarized in Table 7. While the 24 hr reaction gave 90.3% ee and 78.4% yield, the 48 hr reaction gave 96.2% ee and 72.9% yield. In the other three reactions (ACN-41 to ACN-43), TEAB was used as catalyst, and these reactions were run at different temperatures (55-65° C.), Reactions were stopped after 48 hours. High ee% were obtained in all of the three reactions (97-98%).

TABLE 6

Dynamic Kinetic Resolution for Preparation of (2R)-2-Bromo-3-phenylpropanoic Acid -- Initial Reaction Condition Screening.

| Rxn# | Chiral Amine (0.196 mmol) | Catalyst* (5 mg) | Solvent (1 mL) | Time (hr) | Yield$^b$ (%) | e.e. (%) |
|---|---|---|---|---|---|---|
| A-1 | (R)-bornylamine | TBAB | Butylacetate | 24 | 57.79 | 88.5 |
| A-2 | (R)-bornylamine | TBAB | Butylacetate | 48 | 40.00 | 87.0 |

TABLE 6-continued

Dynamic Kinetic Resolution for Preparation of (2R)-2-Bromo-3-phenylpropanoic Acid -- Initial Reaction Condition Screening.

| Rxn# | Chiral Amine (0.196 mmol) | Catalyst* (5 mg) | Solvent (1 mL) | Time (hr) | Yield[b] (%) | e.e. (%) |
|---|---|---|---|---|---|---|
| A-3 | (R)-bornylamine | TMAB | Butylacetate | 48 | 77.19 | 74.3 |
| A-4 | (R)-bornylamine | TEAB | Butylacetate | 48 | 77.59 | 89.4 |
| A-5 | (R)-bornylamine | THAB | Butylacetate | 48 | 42.81 | 89.2 |
| A-6 | (R)-bornylamine | MTOAB | Butylacetate | 48 | 40.00 | 84.5 |
| A-7 | (R)-bornylamine | TOAB | Butylacetate | 48 | 64.75 | 87.6 |
| B-1 | (1S,2R)-2-amino-1,2-diphenylethanol | TBAB | Isobutylacetate/MTBE (2:1 v/v) | 48 | 48.80 | 30.2 |
| B-2 | (1S,2R)-2-amino-1,2-diphenylethanol | TBAB | Isobutylacetate/MTBE (3:1 v/v) | 48 | 41.63 | 31.1 |
| B-3 | (1S,2R)-2-amino-1,2-diphenylethanol | TBAB | Butylacetate/MTBE (2:1 v/v) | 48 | 37.00 | 31.8 |
| B-4 | (1S,2R)-2-amino-1,2-diphenylethanol | TBAB | Isopropylacetate/MTBE (2:3 v/v) | 48 | 65.9 | 28.0 |
| C-1 | (R)-bornylamine | TBAB | Acetonitrile | 48 h | 45.49 | 93.5 |
| C-2 | (R)-bornylamine | TBAB | MTBE | 48 | 78.93 | 85.1 |
| C-3 | (R)-bornylamine | TBAB | Ethyl Acetate | 48 | 69.57 | 88.6 |
| C-4 | (R)-bornylamine | TBAB | THF | 48 | No salt formation | N/A |
| C-5 | (R)-bornylamine | TBAB | Butanol | 48 | 44.15 | 84.1 |
| C-6 | (R)-bornylamine | TBAB | Isobutanol | 48 | 56.19 | 78.1 |

[a]Abbreviations for catalysts are: TBAB tetrabutylammonium bromide; TMAB = tetramethylammonium bromide; TEAB = tetraethylammonium bromide; THAB = tetrahexylammonium bromide; MTOAB = methyltrioctylammonium bromide; TOAB = tetraoctylammonium bromide.
[b]Yield was based on chiral amine.

TABLE 7

Preparation of (2R)-2-Bromo-3-phenylpropanoic Acid through Dynamic Kinetic Resolution and with Acetonitrile as Solvent.

| Rxn # | (R)-bornylamine (mmol) | Catalyst* (20 mg) | Solvent (4 mL) | Temperature (° C.) | Time (hr) | Yield (%) | e.e (%) |
|---|---|---|---|---|---|---|---|
| ACN-1 | 0.782 | TBAB 20 mg | Acetonitrile | 55 | 24 | 78.4 | 90.3 |
| ACN-2 | 0.782 | TBAB 20 mg | Acetonitrile | 55 | 48 | 72.9 | 96.2 |
| ACN-41 | 0.760 | TEAB 16.8 mg | Acetonitrile | 55 | 48 | 72.0 | 98.0 |
| ACN-42 | 0.760 | TEAB 16.8 mg | Acetonitrile | 60 | 48 | 52.0 | 97.8 |
| ACN-43 | 0.760 | TBAB 20 mg | Acetonitrile | 65 | 48 | 52.0 | 97.3 |

EXAMPLE 7

Gram-scale Preparation of (2R)-2-Bromo-3-phenyl-propanoic Acid (VIIR) from Racemic 2-Bromo-3-phenylpropanoic Acid (VII) through Dynamic Kinetic Resolution Gram scale dynamic kinetic resolution reaction of racemic 2-bromo-3-phenylpropanoic acid (VII) was then performed. Thus, under nitrogen, 2-bromoacid VII (3.798 g, 97% pure, 16.00 mmol), (R)-bornylamine (X) (2.400 g, 97% pure, 15.19 mmol) and TEAB (336 mg, 1.58 mmol) were charged into a 200 mL round bottom flask equipped with a magnetic stir bar and a condenser. Acetonitrile (80 mL) was then added. The mixture was then heated to 55° C. The reaction was monitored by chiral HPLC. After 48 hrs,the ee of acid reached 86%. After 72 hrs, an 89.7% ee was observed. The amine-acid salt (VIIRB) obtained after filtration, washing (with 8 mL acetonitrile) and vacuum drying weighed 3.85 g (66.3% yield). This result is also summarized in Table 8 (reaction GR-47).

Four more reactions were run using the same protocol, except that the bornylamine was delivered to the 55° C. reaction mixtures in different speed (from 4.5 hours up to 24 hours) in these reactions, The results were summarized in Table 8 (reactions GR-54, GR-51, GR-52, GR-55). High ee% were obtained from all these four reactions, with the highest ee% corresponding to reaction GR-55, in which bornylamine was added dropwise over 24 hours to the reaction mixture.

The reaction was further scaled up to 6.0 g of bornylamine input. The result is summarized in Table 8 (reaction GR-62). Under the conditions developed and described previously, bornylamine, dissolved in 50 mL acetonitrile, was added through a syringe pump to the reaction mixture at 55° C. over a period of 24 hours. After 48 hours, the reaction was stopped and worked up, A total of 11.33 g of bornylamine-bromoacid salt (VIIRB) was obtained (78.0% yield). The bromo acid VIIR, after separation from bornylamine, had an ee of 95.75%.

TABLE 8

Preparation of (2R)-2-Bromo-3-phenylpropanoic Acid through Dynamic Kinetic Resolution

| Rxn# | Amine (mmol) | Acid mmol | TEAB (mg) | CH$_3$CN (mL) | T (° C.) | Amine Addition Time (hr) | Rxn Time (hr) | Amine-Acid Salt (g) | Yield (%) | ee (%) |
|---|---|---|---|---|---|---|---|---|---|---|
| GR-47 | 15.19 | 16.0 | 336 | 80 | 55 | 0 | 48 | 3.85 | 66.3 | 89.70 |
| GR-54 | 7.60 | 8.00 | 168 | 40 | 55 | 4.5 | 48 | 2.31 | 79.6 | 94.54 |
| GR-51 | 7.60 | 8.00 | 168 | 40 | 55 | 8 | 48 | 2.16 | 74.2 | 94.80 |
| GR-52 | 7.60 | 8.00 | 168 | 40 | 55 | 16 | 48 | 2.16 | 74.4 | 93.13 |
| GR-55 | 7.60 | 8.00 | 168 | 40 | 55 | 24 | 48 | 2.19 | 75.4 | 96.36 |
| GR-62 | 38.0 | 40.0 | 780 | 200 | 55 | 24 | 48 | 11.33 | 78.0 | 95.75 |

EXAMPLE 8

Liberation of (2R)-2-Bromo-3-phenylpropanoic Acid (VIIR) and Recycling and Re-use of (R)-Bornylamine (X)

Different batches of bornylamine-bromoacid salt VIIRB were combined, and a total of 11.61 g (30.36 mmol) of salt (d.e. of the combined salt was ~95%) was used for liberation of (2R)-2- bromo-3-phenylpropanoic acid (VIIR), and for recycling of (R)-bornylamine (X). Thus, the amine-acid salt was mixed with 50 mL of water and 60 mL of MTBE. The pH of the mixture was then adjusted to 1 to 2 with methanesulfonic acid, and was then stirred for 15 min. Layers were separated, and the aqueous layer was extracted with 20 mL MTBE once, then with 10 mL MTBE twice. Organic layers were combined and washed with 5 mL water, then with 10 mL brine, and then dried over MgSO$_4$. Chiral HPLC analysis showed that the acid VIIR in MTBE had an ee of 94.71%. The organic layer was used directly to synthesize (2S)-2-acetylthio-3-phenylpropanoic acid (VIII) (Example 10).

Bornylamine (X) was recycled by first adjusting the pH of the aqueous solution of bornylamine-methane sulfonic acid (XM), obtained from the previous step, to 10-13, and then extracting the free amine into MTBE. After removal of solvent, 4.308 g of (R)-bornylamine (X) was obtained (>97% pure by $^1$H NMR, 92.6% yield).

The recycled bornylamine (X) was used in the dynamic kinetic resolution reaction of racemic 2-bromo-3-phenylpropanoic acid (VII). Thus, 7.60 mmol bornylamine (X) was dissolved in 10 mL acetonitrile, and was added through a syringe pump to the reaction mixture of 8.0 mmol bromo acid, 168 mg TEAB in 30 mL acetonitrile at 55° C. over a period of 24 hours. After 48 hours, the reaction was stopped and worked up. A total of 2.1 g of bornylamine-bromoacid salt (VIIRB) was obtained (72.3% yield). The bromo acid (VIIR), after separation from bornylamine, has an ee of 91.80%.

EXAMPLE 9

Preparation of (2R)-2-Bromo-3-phenylpropanoic Acid (VIIR) from (2S)-2-Bromo-3-phenylpropanoic Acid (VIIS) through Dynamic Kinetic Resolution The reaction of direct conversion of (2S)-2-bromo-3-phenylpropanoic acid (VIIS) to (2R)-2-bromo-3-phenylpropanoic acid (VIIR) through dynamic resolution was performed (Table 9). Thus, 7.60 mmol bornylamine (X) was dissolved in 10 mL acetonitrile, and was added through a syringe pump to the reaction mixture of 8.0 mmol (2S)-2-bromo-3-phenylpropanoic acid (VIIS), 168 mg TEAB in 30 mL acetonitrile at 55° C. over a period of 16 hours. After 48 hours the reaction was stopped and worked up. A total of 2.07 g of bornylamine-bromoacid salt (VIIRB) was obtained (71.2% yield). The bromo acid, after separation from bornylamine (X), had an ee of 95.80%.

TABLE 9

Dynamic Kinetic Resolution for Preparation of (2R)-2-Bromo-3-phenylpropanoic Acid

| Rxn | Amine mmol | Acid (mmol) | TEAB (mg) | CH$_3$CN (mL) | T (° C.) | Amine Addition Time (hr) | Rxn Time (hr) | Amine-Acid Salt (g) | Yield (%) | ee (%) |
|---|---|---|---|---|---|---|---|---|---|---|
| DR-61 | 7.60 | 8.00 | 168 | 40 | 55 | 16 | 48 | 2.07 | 71.2 | 95.8 |

EXAMPLE 10

Preparation of (2S)-2-Acetylthio-3-phenylpropanoic acid (VIII) from (2R)-2-Bromo-3-phenylpropanoic acid (VIIR)

(2R)-2-Bromo-3-phenylpropanoic acid (VIIR) (94.71% ee, ~30.36 mmol)-MTBE solution obtained from Example 8 was concentrated to 30 mL, and then was transferred into a 100 mL 3-neck round bottom flask equipped with mechanical stirring and thermometer. KSAc (3.538 g, 30.36 mmol) was slowly added to the flask over 5 minutes. A water bath was used to keep the reaction temperature below 30° C. The mixture was stirred for 24 hours. Water (10 g) was added, and the mixture was stirred for 10 minutes. Layers were separated, the organic layer was washed with 6 wt % Na₂S₂O₃ solution (twice, 10 g each time), and then washed with brine (10 g). After removal of solvent, an oily product was obtained. The oily product solidified after cooling down to 0° C. A total of 6.40 g of product (VIII) was obtained (83.33 M% product, 16.67 M% MTBE by ¹H NMR, 87.1% yield after correction for MTBE), and the ee of the product was 92.4%.

Crystallization of (2S)-2-Acetylthio-3-phenylpropanoic Acid (VIII)

Crude (2S)-acetylthio-3-phenylpropanoic acid (VIII) (8.29 g, 88.4%) was dissolved in MTBE (4 mL, 1.4 mL/g). The solution of acid in MTBE was then heated to 45° C. Heptane (25 mL) was added dropwise to the warm solution until cloudy. The slurry was seeded with (2S)-acetylthio-3-phenylpropanoic acid crystal, and slowly cooled to room temperature without agitation. The addition of heptane was continued (15 mL) with agitation over 30 min. The solid (5.5 g) was collected via vacuum filtration after chilling in ice/water bath, and washed with cold heptane. The purified (2S)-acetylthio-3-benzenepropanoic acid (VIII) was assayed by HPLC to determine the purity, at yield 66%, ee was 98.7% (purity 98.2%).

EXAMPLE 11

Preparation of (R)-α-(Benzoylthio)-3,4,4-Trimethyl-2,5-Dioxo-1-Imidazolidinebutanoic Acid Directly From Its Racemic Precursor

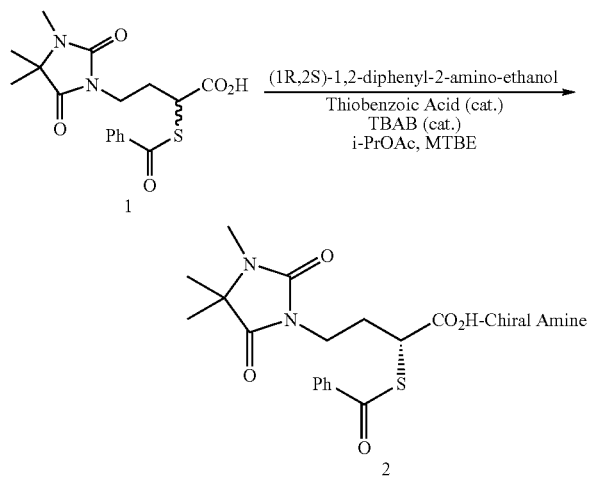

Racemic α-(benzoylthio)-3,4,4-trimethyl-2,5-dioxo-1-imidazolidinebutanoic acid (1, 1.00 eq.), (1R,2S)-1,2-diphenyl-2-aminoethanol (0.95-1.00 eq.), tetrabutylammonium bromide (0.03 eq.) and thiobenzoic acid (0.02-0.04 eq.) were heated to 55-60° C. for 84 h in a mixture of MTBE and i-PrOAc (1:1, 0.26M based on input carboxylic acid). The mixture was cooled to RT and the resolved salt was isolated by filtration. A sample of the salt was dissolved in a solution of EtOH/1 vol % THF and analyzed by chiral HPLC. The enriched R-diastereomeric salt (2) was obtained as a white solid in 85% yield in a 94.3:5.7 ratio of diastereomers.

EXAMPLE 12

Preparation of (S-α-(Benzoylthio)-3,4,4-Trimethyl-2,5-Dioxo-1-Imidazolidinebutanoic Acid Directly From Its Racemic Precursor Racemic α-(benzoylthio)-3,4,4-trimethyl-2,5-dioxo-1-imidazolidinebutanoic acid (1, 1.00 eq.), (1S,2R)-1,2-diphenyl-2-aminoethanol (chiral amine, 1.05 eq.), tetrabutylammonium bromide (0.03 eq.) and thiobenzoic acid (0.02-0.04 eq.) were heated to 55-60° C. for 15 h in a mixture of MTBE and i-PrOAc (1:1, 0.26 M based on input carboxylic acid). The mixture was cooled to RT and the resolved salt was isolated by filtration. A sample of the salt was dissolved in a solution of EtOH/1 vol % THF and analyzed by chiral HPLC. The enriched S-diastereomeric salt was obtained as a white solid in 80.8% yield in a 84.7:15.3 ratio of diastereomers.

EXAMPLE 13

α-Bromo-3,4,4-trimethyl-2,5-dioxo-1-imidazolidinebutanoic acid salt Polymorph Identification Two different polymorphs (a.k.a., crystal forms), I and II, of the α-Bromo-3,4,4-trimethyl-2,5-dioxo-1-imidazolidinebutanoic acid salt were identified using Raman as well as X-ray powder diffraction spectroscopy.

Figure 2:
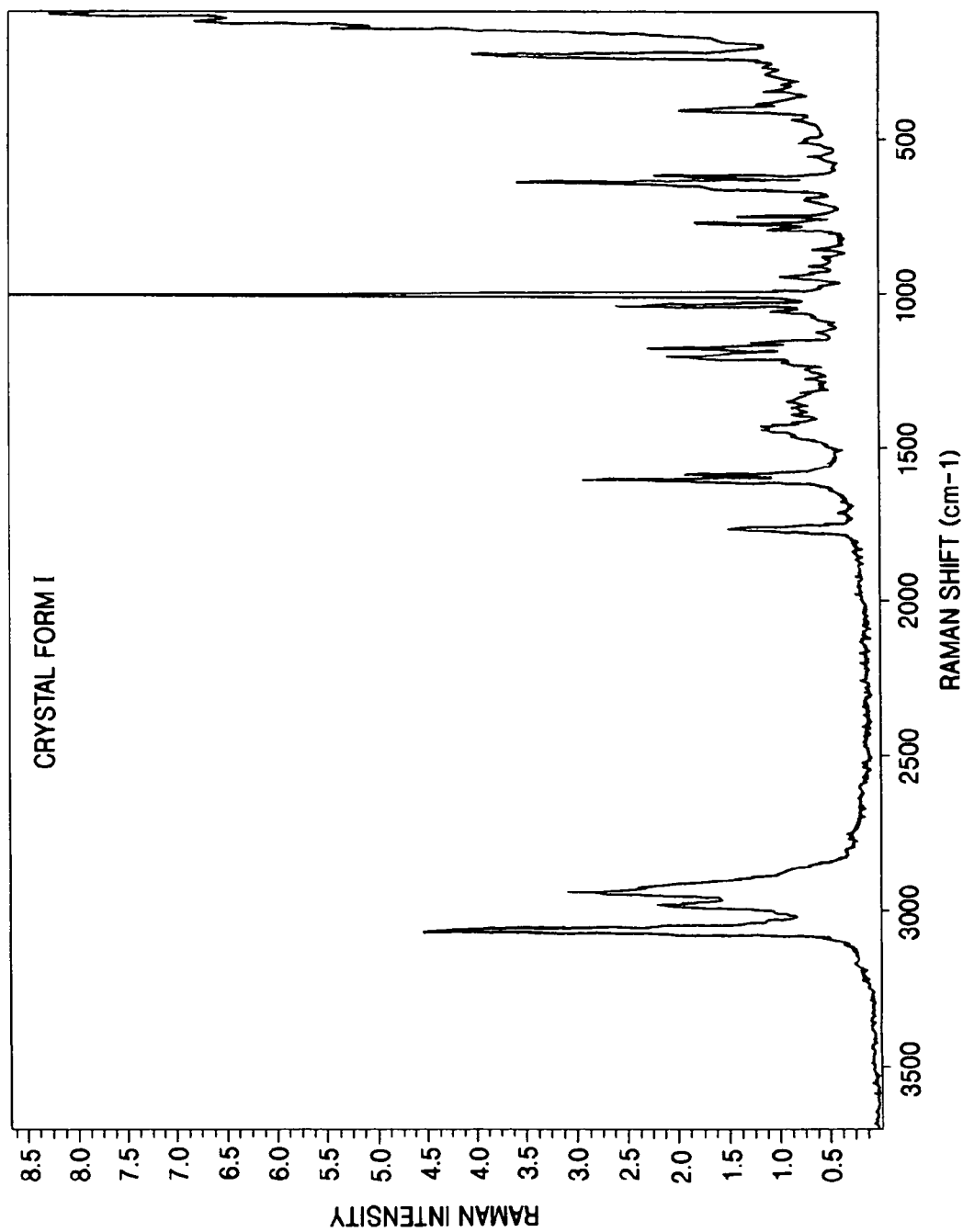
FIG. 2 shows the Raman spectrum of polymorph form I of the salt of α-Bromo-3,4,4-trimethyl-2,5-dioxo-1-imidazolidinebutanoic acid.
Figure 3:
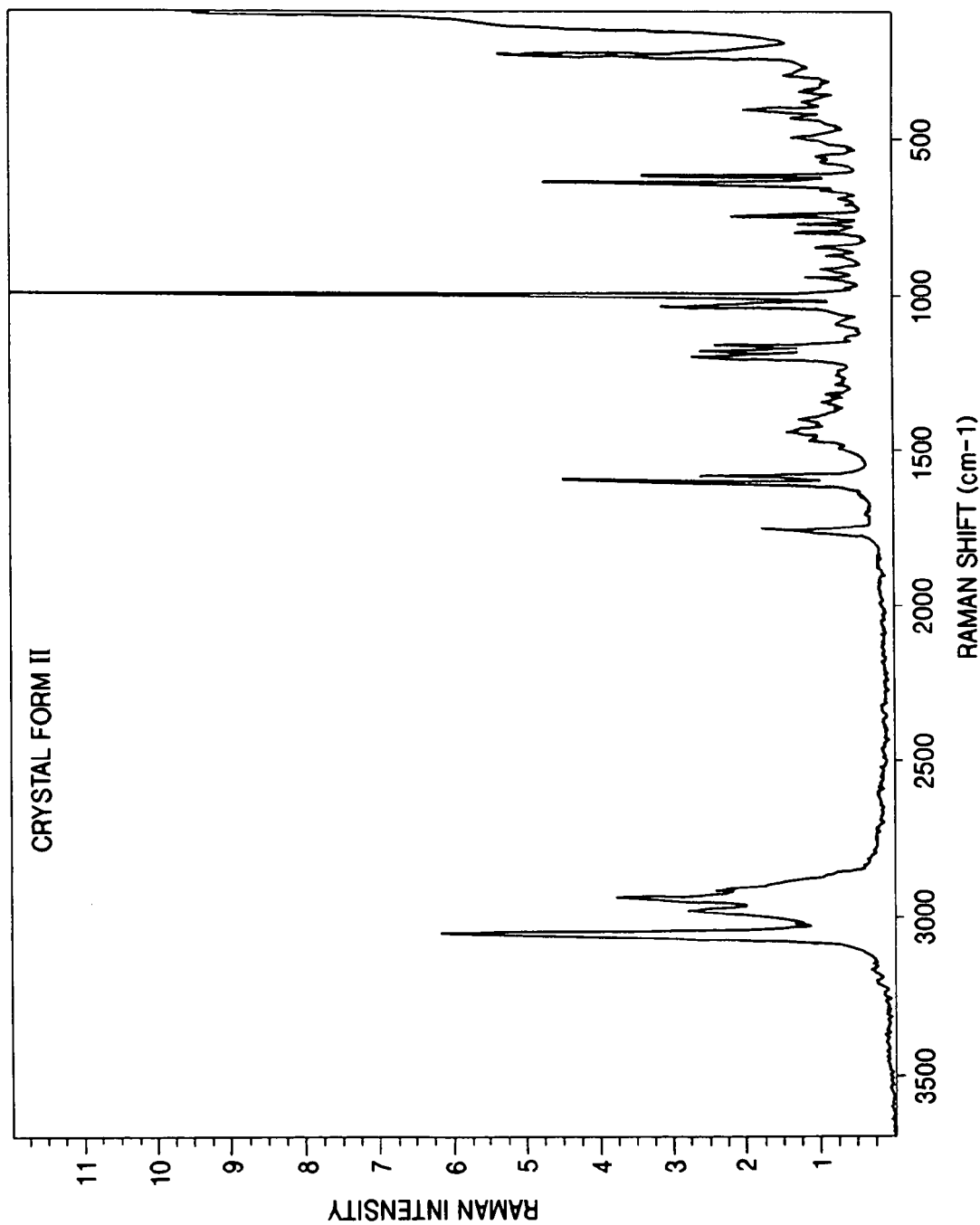
FIG. 3 shows the Raman spectrum of polymorph form II of the salt of α-Bromo-3,4,4-trimethyl-2,5-dioxo-1-imidazolidinebutanoic acid.

Upon mixing the chiral amine with the racemic α-Bromo-3,4,4-trimethyl-2,5-dioxo-1-imidazolidinebutanoic acid either one of the two polymorph forms, or a mixture of both, were formed. Polymorph Form I and II of the salt of α-Bromo-3,4,4-trimethyl-2,5-dioxo-1-imidazolidinebutanoic acid was determined by standard X-Ray powder diffraction (FIG. 1). Similarly, using standard Raman spectroscopy techniques, polymorph forms I and II were identified (see FIGS. 2 and 3 respectively).

In general, kinetic conditions=low temperature, less polar solvent favor form II, while thermodynamic conditions=high temperature, polar solvent and the presence of form I seeds favor the form I.

To produce the preferred polymorph form I, temperatures in the range of about 50° C. to about 70° C. are preferred. More preferably, the temperature should be from 60° C. to about 65° C. Preferred polar solvents include, but are not limited to, ethylacetate and isopropylacetate.

EXAMPLE 14

Figure 4:
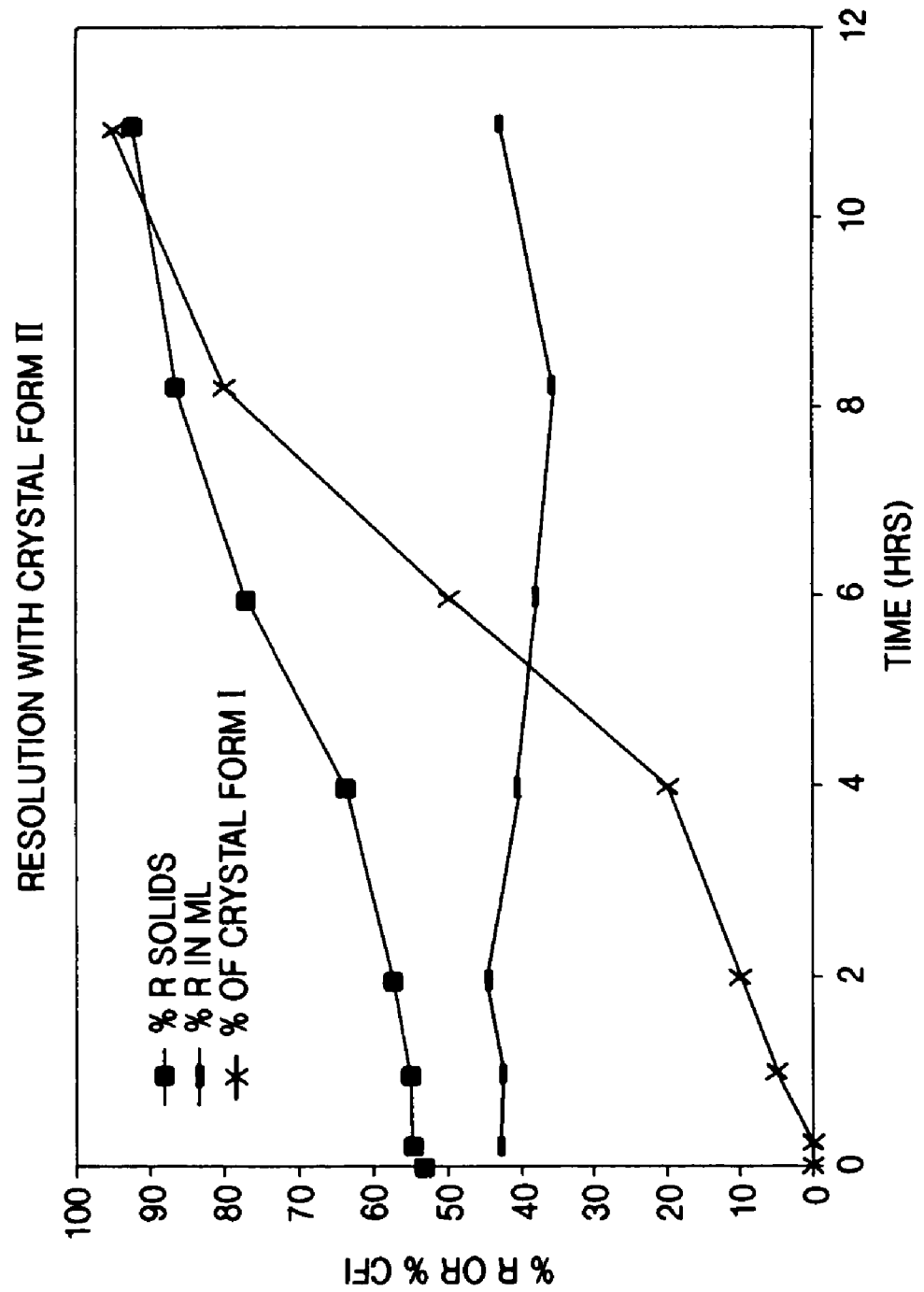
FIG. 4 shows the results of Dynamic Resolution carried out with pre-prepared diastereomeric salt of pure α-Bromo-3,4,4-trimethyl-2,5-dioxo-1-imidazolidinebutanoic acid polymorph form II.
Figure 5:
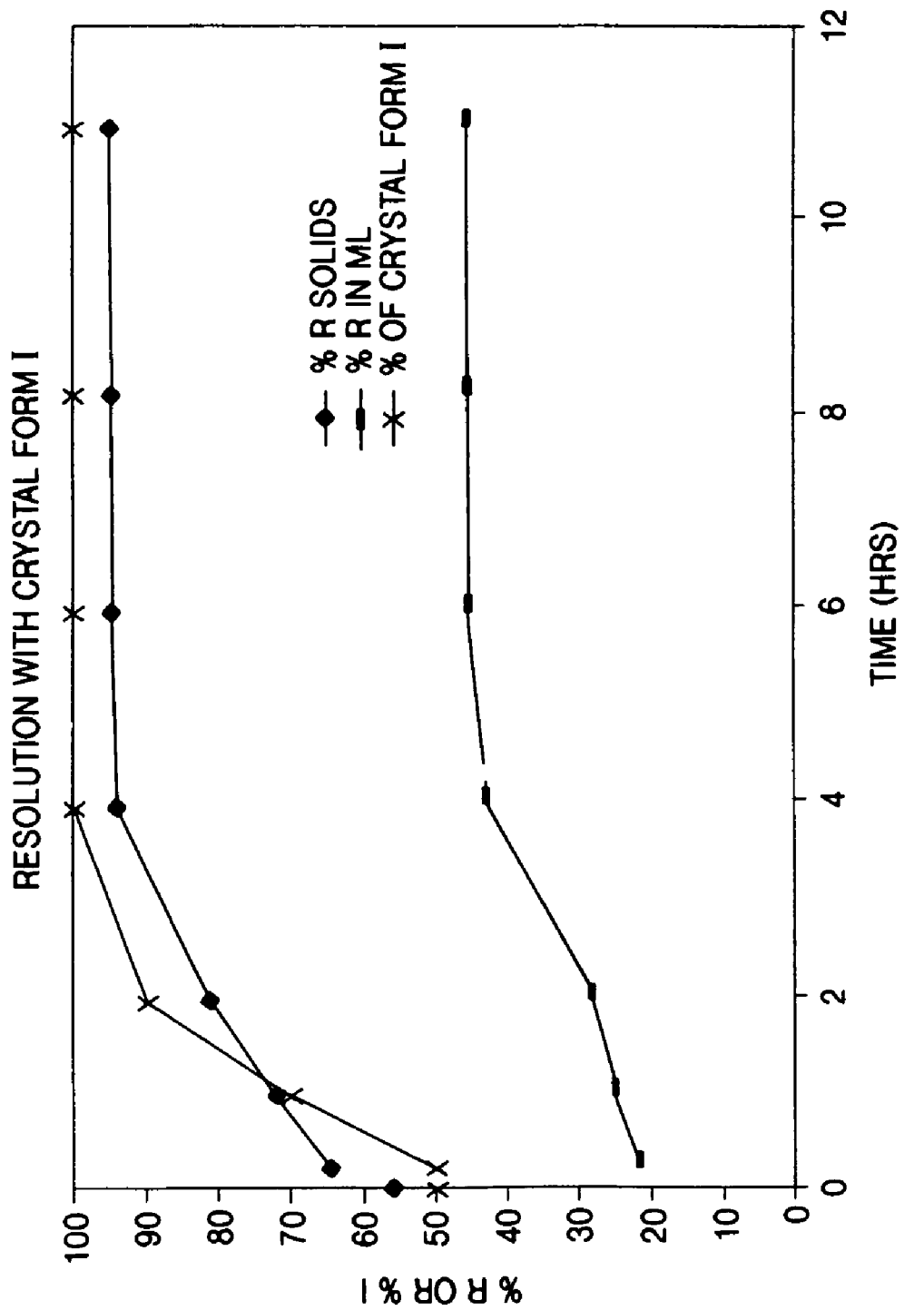
FIG. 5 shows the results of Dynamic Resolution carried out with a mixture of α-Bromo-3,4,4-trimethyl-2,5-dioxo-1-imidazolidinebutanoic acid salt polymorph forms I and II.

Effect of α-Bromo-3,4,4-trimethyl-2,5-dioxo-1-imidazolidinebutanoic acid Salt Polymorphs on the Dynamic Resolution Dynamic Resolutions were carried out with pre-prepared diastereomeric salt of pure α-Bromo-3,4,4-trimethyl-2,5-dioxo-1-imidazolidinebutanoic acid polymorph form II (FIG. 4) and a mixture of α-Bromo-3,4,4-trimethyl-2,5-dioxo-1-imidazolidinebutanoic acid polymorph forms I and II (FIG. 5). Periodically samples of the slurries were drawn and filtered by centrifugation. The chiral ratio of the mother liquor and the precipitated salt were determined by chiral HPLC and the polymorph composition of the solids was dertermined by Raman assay. The progress of the two reactions was monitored as the enhancement of R-enantiomer of the bromoacid in the precipitated salt.

When the Dynamic Resolution process was attempted using 100% of polymorph II, no enhancement of the R-enantiomer in the precipitated salt could be observed for 4 hours. The chiral ratio of the mother liquor was 45% R and 55% S, pointing to a nearly equal solubility of the two diastereomers. Within this time the polymorph composition of the precipitated salt changed from 100% II to 80% II with 20% I. After 2 hours the R enantiomer started to increase, accompanied by a further change of the polymorph composition. After 11 hours the salt contained 92% of the R-enantiomer and consisted of 95% of polymorph I.

When the Dynamic Resolution process was run with 50% of polymorph I and 50% of polymorph II, the amount of R-enantiomer in the precipitated salt increased linearly right from the beginning. The chiral ratio of the mother liquor was 25% R and 75% S, pointing to a significant difference in the solubility of the two diastereomers. Within this time the polymorph composition of the precipitated salt changed from 50% I with 50% II to 100% I. After 4 hours the salt contained 94% of the R-enantiomer.

Hence, it was determined that complete Resolution to about 95:5 (RRS:SRS) only occurs in presence of crystal form I whereas in the presence of polymorph form II, the resolution stalls at a diastereomeric ratio of about 60:40 (RRS:SRS).

EXAMPLE 15

∝-Bromo-3,4,4-trimethyl-2,5-dioxo-1-imidazolidinebutanoic acid Polymorph Conversion The diasteromeric salt was prepared by mixing racemic ∝-Bromo-3,4,4-trimethyl-2,5-dioxo-1-imidazolidinebutanoic acid at 0.13 M concentration with 1.0 eq of the chiral amine in the indicated solvent at room temperature. The resulting slurry was then heated to 65° C. Periodically samples of the precipitate were taken and the polymorph composition determined by Raman spectroscopy. Table 10 shows the solvent and temperature dependence of the conversion of polymorph form II to form I.

TABLE 10

Polymorphs (0.13 M slurries of racemic diastereomeric salt heated to 65° C.)

| Solvent | 0 h | 0.5 h | 1.0 h | 1.5 hrs | 15.5 hrs |
|---|---|---|---|---|---|
| EtOAc | II (100%) | I (100%) | I (100%) | — | — |
| heptane | II (100%) | II (98%) + I (2%) | II (95%) + I (5%) | II (90%) + I (10%) | I (100%) |
| 1:1 EtOAc heptane | II (100%) | II (100%) | II (100%) | II (100%) | II (100%) |

While Crystal Form II was seen to convert to Crystal Form I, Crystal Form I was not observed to convert into crystal from II.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A dynamic resolution method of enriching a desired isomer of a racemic alpha-substituted carboxylic acid relative to an undesired isomer, the method comprising:

1) in a solvent, contacting the racemic alpha-substituted carboxylic acid, wherein the alpha substitution is with a leaving group which is selected from the group consisting of a chloride, a bromide, an iodide, an alkanoate, a benzoate, a thioalkanoate, a thiobenzoate, a thiolate, a silyl alcoholate, an azide and a cyanide, and wherein the alpha carbon is chiral, with a homochiral amine to form a salt that is partially insoluble under selected reaction conditions, wherein the homochiral amine is selected so that the solubility of the amine salt of the undesired alpha-substituted carboxylic acid is greater than that of the amine salt of the desired alpha-substituted carboxylic acid under the selected reaction conditions;

2) reacting under the selected reaction conditions the salt from step 1) with a nucleophile which is an anion salt selected from the group consisting of a chloride, a bromide, an iodide, an alkanoate, a benzoate, a thioalkanoate, a thiobenzoate, a thiolate, a silyl alcoholate, an azide and a cyanide, wherein the reacting is effective in producing a net increase in the less soluble amine salt of the alpha-substituted carboxylic acid, and wherein the reaction conditions are selected to (a) promote nucleophilic substitution of the nucleophile and the leaving group or (b) to produce the increase in the less soluble amine salt in the absence of a strong base; and 3) maintaining the reaction to increase the amount of the desired alpha-substituted carboxylic acid isomer.

2. The method of claim 1, wherein the reaction conditions are selected to (a) promote nucleophilic substitution of the anion and the leaving group.

3. The method of claim 1, wherein the reaction conditions are selected to (b) produce the increase in the less soluble amine salt in the absence of a strong base.

4. The method of claim 1, wherein the nucleophile is the anion equivalent of the leaving group.

5. The method of claim 1, wherein the reaction occurs without substantial substitution of the leaving group with the amine group of the homochiral amine such that no more than 0-5% of the alpha-substituted carboxylic acid is consumed in a side reaction.

6. A method of preparing an alpha-substituted carboxylic acid formed by reaction with a nucleophile which is an anion salt selected from the group consisting of a chloride, a bromide, an iodide, an alkanoate, a benzoate, a thioalkanoate, a thiobenzoate, a thiolate, a silyl alcoholate, an azide and a cyanide; reaction with a homochiral amine; substitution of a leaving group selected from the group consisting of a chloride, a bromide, an iodide, an alkanoate, a benzoate, a thioalkanoate, a thiobenzoate, a thiolate, a silyl alcoholate, an azide and a cyanide, and contacting with the leaving group to provide alpha-substitution; comprising:
  (a) conducting the method of claim 1 to obtain at least 80% ee in the alpha-substituted carboxylic acid; and
  (b) isolating the alpha-substituted carboxylic acid, or an acid adduct thereof formed by reacting the alpha-substituted carboxylic acid as the nucleophile, or reacting the alpha-substituted carboxylic acid in a subsequent reaction.

7. The method of claim 6, further comprising
  (c) reacting the alpha-substituted carboxylic acid with the nucleophile which is an anion salt selected from the group consisting of a chloride, a bromide, an iodide, an alkanoate, a benzoate, a thioalkanoate, a thiobenzoate, a thiolate, a silyl alcoholate, an azide and a cyanide, to replace the leaving group with the nucleophile.

8. The method of claim 6 or claim 7, further comprising subsequent to step (a) or step (c), reacting the carboxylic acid moiety to form an amide bond.

9. A dynamic resolution method of enriching a desired isomer of an alpha-substituted carboxylic acid relative to an undesired isomer, the method comprising:
   in a solvent, contacting the alpha-substituted carboxylic acid, wherein the alpha substitution is with a leaving group which is selected from the group consisting of a chloride, a bromide, an iodide, an alkanoate, a benzoate, a thioalkanoate, a thiobenzoate, a thiolate, a silyl alcoholate, an azide and a cyanide, and wherein the alpha carbon is chiral, with a homochiral amine to form a salt; said homochiral amine being selected so that the solubility of the amine salt of the undesired alpha-substituted carboxylic acid is greater than that of the amine salt of the desired alpha-substituted carboxylic acid under selected reaction conditions;
   identifying a first solid crystalline phase of said salt;
   determining the difference in solubility of the diastereomers of said first solid crystalline phase;
   increasing the difference in solubility of said diastereomers by converting said first solid crystalline phase into a second solid crystalline phase by slurrying said first solid crystalline phase in a solvent at elevated temperatures;
   reacting under said selected reaction conditions said salt with a nucleophile which is an anion salt selected from the group consisting of a chloride, a bromide, an iodide, an alkanoate, a benzoate, a thioalkanoate, a thiobenzoate, a thiolate, a silyl alcoholate, an azide and a cyanide, wherein the reacting is effective in producing a net increase in the less soluble amine salt of the alpha-substituted carboxylic acid, and wherein said reaction conditions are selected to (a) promote nucleophilic substitution of the nucleophile and the leaving group, or (b) to produce the increase in the less soluble amine salt in the absence of a strong base; and
   maintaining the reaction to increase the amount of the desired alpha-substituted carboxylic acid isomer.

10. A method of dynamically resolving 3,4,4-trimethyl-2,5-dioxo-1-imidazolidinebutanoic acid alpha-substituted with a leaving group which is selected from the group consisting of a chloride, a bromide, an iodide, an alkanoate, a benzoate, a thioalkanoate, a thiobenzoate, a thiolate, a silyl alcoholate, an azide and a cyanide, the method comprising:
   in a solvent, contacting the alpha-substituted 3,4,4-trimethyl-2,5-dioxo-1-imidazolidinebutanoic acid, with a homochiral amine to form a salt that is partially insoluble under selected reaction conditions, wherein the homochiral amine is selected so that the solubility of a desired isomer of the alpha-substituted 3,4,4-trimethyl-2,5-dioxo-1-imidazolidinebutanoic acid is less than that of an opposite isomer under the selected reaction conditions;
   reacting, under the selected reaction conditions, the salt with a nucleophile which is an anion salt selected from the group consisting of a chloride, a bromide, an iodide, an alkanoate, a benzoate, a thioalkanoate, a thiobenzoate, a thiolate, a silyl alcoholate, an azide and a cyanide, wherein the reacting is effective in producing a net increase in the less soluble amine salt of the alpha-substituted carboxylic acid, and wherein the reaction conditions are selected to (a) promote nucleophilic substitution of the nucleophile and the leaving group or (b) to produce the increase in the less soluble amine salt in the absence of a strong base; and
   maintaining the reaction to increase the amount of the desired isomer of alpha-substituted 3,4,4-trimethyl-2,5-dioxo-1-imidazolidinebutanoic acid.

11. The method of claim 10, wherein at least 80% ee in the R★-isomer of alpha-substituted 3,4,4-trimethyl-2,5-dioxo-1-imidazolidinebutanoic acid is obtained.

12. The method of claim 10, wherein the homochiral amine is (1R,2S)-(−)-2-amino-1,2-diphenylethanol.

13. The method of claim 10, wherein the nucleophile is introduced into the dynamic resolution reaction as a tetralkylammonium bromide.

14. A method of dynamically resolving 3-phenylpropanoic acid alpha-substituted with a leaving group which is selected from the group consisting of a chloride, a bromide, an iodide, an alkanoate, a benzoate, a thioalkanoate, a thiobenzoate, a thiolate, a silyl alcoholate, an azide and a cyanide, the method comprising:
   in a solvent, contacting the alpha-substituted 3-phenylpropanoic acid, with a homochiral amine to form a salt that is partially insoluble under selected reaction conditions, wherein the homochiral amine is selected so that the solubility of a desired isomer of the alpha substituted 3-phenylpropanoic acid is less than that of an opposite isomer under the selected reaction conditions;
   reacting, under the selected reaction conditions, the salt with a nucleophile which is an anion salt selected from the group consisting of a chloride, a bromide, an iodide, an alkanoate, a benzoate, a thioalkanoate, a thiobenzoate, a thiolate, a silyl alcoholate, an azide and a cyanide, where the nucleophile is the anion equivalent of the leaving group, under conditions selected to promote nucleophilic substitution of the nucleophile and the leaving group; and
   maintaining the reaction to increase the amount of the desired isomer of alpha-substituted 3-phenylpropanoic acid.

15. A compound selected from:
   (R) or (S)-α-bromo-3,4,4-trimethyl-2,5-dioxo-1-imidazolidinebutanoic acid as a salt with a homochiral amine which is not quinine; or
   (R) or (S)-α-(benzoylthio)-3,4,4-trimethyl-2,5-dioxo-1-imidazolidinebutanoic acid as a salt with a homochiral amine which is not quinine.

16. A compound selected from:
   (R)-α-bromo-3,4,4-trimethyl-2,5-dioxo-1-imidazolidinebutanoic acid in at least 85% ee; or
   (S)-α-(benzoylthio)-3,4,4-trimethyl-2,5-dioxo-1-imidazolidinebutanoic acid in at least 98% ee; or
   a pharmaceutically acceptable salt thereof.

17. A method of preparing (2R)-2-bromo-3-phenylpropanoic acid from (L)-phenylalanine, the method comprising:
   (a) converting (L)-phenylalanine to form (2S)-2-bromo-3-phenylpropanoic acid;
   (b) contacting (2S)-2-bromo-3-phenylpropanoic acid in a solvent with a homochiral amine to form a salt that is partially insoluble under selected reaction conditions, wherein the homochiral amine is selected so that the solubility of the amine salt of the (2S)-2-bromo-3-phenylpropanoic acid is greater than that of the amine salt of the (2R)-2-bromo-3-phenylpropanoic acid under the selected reaction conditions;
   (c) reacting under the selected reaction conditions the amine salts with a bromide, wherein the reacting is effective in producing a net increase in the amine salt of (2R)-2-bromo-3-phenylpropanoic acid, and wherein the selected conditions are selected to (i) promote nucleophilic racemization of (2S)-2-bromo-3-phenylpropanoic acid or (ii) produce the increase in (2R)-2-bromo-3-phenylpropanoic acid in the absence of a strong base; and (d) maintaining the reaction to increase the amount of (2R)-2-bromo-3-phenylpropanoic acid.

18. The method of claim 17, wherein the solvent in step (b) is acetonitrile, tetrahydrofuran, ethyl acetate, butyl acetate, n-butanol, methyl tert-butyl ether or methyl isobutyl ketone.

19. The method of claim 17, wherein the homochiral amine is (R)-bornylamine.

20. The method of claim 17, wherein the bromide is introduced into the dynamic resolution reaction as a tetralkylammonium bromide.

21. A method of preparing a desired enantiomer of an alpha substituted carboxylic acid from an amino acid, the method comprising:

(a) converting an undesired enantiomer of an alpha-amino carboxylic acid to form an undesired enantiomer of an alpha-substituted carboxylic acid, wherein the alpha substitution is with a leaving group which is selected from the group consisting of a chloride, a bromide, an iodide, an alkanoate, a benzoate, a thioalkanoate, a thiobenzoate, a thiolate, a silyl alcoholate, an azide and a cyanide, and the alpha carbon is chiral;

(b) contacting the undesired enantiomer of the alpha-substituted carboxylic acid with a homochiral amine to form a salt that is partially insoluble under selected reaction conditions, wherein the homochiral amine is selected so that the solubility of the amine salt of the undesired enantiomer is greater than that of the amine salt of the desired enantiomer under the selected reaction conditions;

(c) reacting under the selected reaction conditions the amine salts with a nucleophile which is an anion selected from the group consisting of a chloride, a bromide, an iodide, an alkanoate, a benzoate, a thioalkanoate, a thiobenzoate, a thiolate, a silyl alcoholate, an azide and a cyanide, wherein the reacting is effective in producing a net increase in the amine salt of the desired enantiomer of the alpha-substituted carboxylic acid, and wherein the reaction conditions are selected to (i) promote nucleophilic substitution of the nucleophile and the leaving group or (ii) produce the increase in the desired enantiomer of the alpha-substituted carboxylic acid in the absence of a strong base; and (d) maintaining the reaction to increase the amount of the desired enantiomer of the alpha-substituted carboxylic acid.

* * * * *